US009642859B2

(12) United States Patent
Gonzales

(10) Patent No.: US 9,642,859 B2
(45) Date of Patent: May 9, 2017

(54) USE OF CAPSAZEPINE AND ANALOGS THEREOF TO TREAT CANCER

(71) Applicant: THE BOARD OF REGENTS OF THE UNIVERSITY OF TEXAS SYSTEM, Austin, TX (US)

(72) Inventor: Cara B. Gonzales, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/649,272

(22) PCT Filed: Dec. 3, 2013

(86) PCT No.: PCT/US2013/072857
§ 371 (c)(1),
(2) Date: Jun. 3, 2015

(87) PCT Pub. No.: WO2014/089067
PCT Pub. Date: Jun. 12, 2014

(65) Prior Publication Data
US 2015/0352123 A1  Dec. 10, 2015

Related U.S. Application Data

(60) Provisional application No. 61/732,511, filed on Dec. 3, 2012.

(51) Int. Cl.
| | |
|---|---|
| *A61K 31/55* | (2006.01) |
| *A61K 9/19* | (2006.01) |
| *A61K 45/06* | (2006.01) |
| *A61P 35/00* | (2006.01) |
| *A61K 9/00* | (2006.01) |

(52) U.S. Cl.
CPC ............ *A61K 31/55* (2013.01); *A61K 9/0019* (2013.01); *A61K 45/06* (2013.01)

(58) Field of Classification Search
CPC ....... A61K 31/55; A61K 9/0019; A61K 45/06
See application file for complete search history.

(56) References Cited

U.S. PATENT DOCUMENTS

| | | | |
|---|---|---|---|
| 5,403,868 A | 4/1995 | Reid et al. | 14/94 |
| 7,514,562 B2 | 4/2009 | Fell et al. | 546/276.4 |
| 7,906,508 B2 | 3/2011 | Koga et al. | 514/230.5 |
| 8,008,292 B2 | 8/2011 | Koga et al. | 514/230.5 |
| 2006/0035939 A1 | 2/2006 | Koga et al. | 514/355 |

OTHER PUBLICATIONS

Sanchez, "Induction of apoptosis in prostate tumor PC-3 cells and inhibition of xenograft prostate tumor growth by the vanilloid capsaicin", Apoptosis, 2006; 11, pp. 89-99.*

Tong, "Tumor Tissue-Derived Formaldehyde and Acidic Microenvironment Synergistically Induce Bone Cancer Pain", PLoS ONE, Apr. 2010, 5, e10234, pp. 1-15.*
Bevan S., Hothi S. et al. "Capsazepine: a competitive antagonist of the sensory neurone excitant capsaicin," *Br. J Pharmacal.* 107: 544-552, 1992.
Deeds, et al., "Patterns of melastatin mRNA expression in melanocytic tumors," *Hum. Pathol.* vol. 31, 2000, pp. 1346-1356.
Domotor, et al., "Immunohistochemical distribution of vanilloid receptor, calcitonin-gene related peptide and substance P in gastrointestinal mucosa of patients with different gastrointestinal disorders." *Inflammopharmacology*, vol. 13, 2005, pp. 161-177.
Duncan, et al., "Melastatin expression and prognosis in cutaneous malignant melanoma," *J Clin. Oneal.* vol. 19, 2001, pp. 568-576.
Duncan, et. al., "Down-regulation of the novel gene melastatin correlates with potential for melanoma metastasis," *Cancer Res.* vol. 58, 1998, pp. 1515-1520.
Fang et al., "Expression and Up-regulation of alternatively spliced transcripts of melastatin, a melanoma metastasis-related gene, in human melanoma cells," *Biochem. Biophys. Res. Commun.* vol. 279, 2000, pp. 53-61.
Fixemer, et al., "Expression of the Ca2+-selective cation channel TRPV6 in human prostate cancer: a novel prognostic marker for tumor progression," *Oncogene* 22: 7858-7861, 2003.
Fuessel, et al., "Multiple tumor marker analyses (PSA, hK2, PSCA, trp-p8) in primary prostate cancers using quantitative RT-PCR," *Int. J Oneal.* vol. 23, 2003, pp. 221-228.
Bartel, et al., "Vanilloids in pancreatic cancer: potential for chemotherapy and pain management," *Gut.* 55: 519-528, 2006.
Lazzeri, et al., "Transient receptor potential vanilloid type 1 (TRPV1) expression changes from normal urothelium to transitional cell carcinoma of human bladder," *Eur. Ural.* vol. 48, 2005, pp. 691-698.
Mergler, et al., "Transient receptor potential channel TRPM8 agonists stimulate calcium influx and neurotensin secretion in neuroendocrine tumor cells," *Neuroendocrinology* 85:81-92, 2007.
Peng, et al., "Human calcium transport protein CaT1," *Biochem. Biophys. Res. Commun.* vol. 278, 2000, pp. 326-332.
Peng, et al., "CaT1 expression correlates with tumor grade in prostate cancer," *Biochem. Biophys. Res. Commun.* vol. 282, 2001, pp. 729-734.
Prevarskaya, et al., "TRP channels in cancer," *Biochica et Biophysica Acta.* 1772: 937-46, 2007a.
Prevarskaya, et al., "Ion channels in death and differentiation of prostate cancer cells," *Cell Death and Differentiation* 14: 1295-1304, 2007b.
Reilly, et al., "Capsaicinoids cause inflammation and epithelial cell death through activation of vanilloid receptors," *Toxicol Sci.* 73(1): 170-81, 2003.
Sanchez, et al., "Expression of the transient receptor potential vanilloid 1 (TRPV1) in LNCaP and PC-3 prostate cancer cells and in human prostate tissue," *Eur. J Pharmacal.* vol. 515, 2005, pp. 20-27.

(Continued)

*Primary Examiner* — Sahar Javanmard
(74) *Attorney, Agent, or Firm* — Norton Rose Fulbright US LLP

(57) ABSTRACT

Disclosed are methods and compositions for treating cancer, particularly for reducing cancerous cell growth, for example, in solid tumors. Disclosed methods and compositions include capsazepine (CPZ) or an analog of CPZ. Compositions comprising CPZ or an analog of CPZ may be useful for simultaneously treating cancer and alleviating pain by blocking TRPV1 channels.

17 Claims, 38 Drawing Sheets

(56) References Cited

OTHER PUBLICATIONS

Szallasi, et al., "The vanilloid receptor TRPV1: 10 years from channel cloning to antagonist proof-of-concept," *Nature Reviews Drug* Discovery, vol. 6, 2007, pp. 357-372.
Tsavaler, et al., "Trp-p8, a novel prostate-specific gene, is up-regulated in prostate cancer and other malignancies and shares high homology with transient receptor potential calcium channel proteins," *Cancer Res.* 61: 3760-3769, 2001.
Wissenbach, et al., "TRPV6 and prostate cancer: cancer growth beyond the prostate correlates with increased TRPV6 Ca2+ channel expression," *Biochem. Biophys. Res. Commun.* vol. 322, 2004, pp. 1359-1363.
Zhuang, et al., "Calcium-selective ion channel, CaT1, is apically in gastrointestinal tract epithelia and is aberrantly expressed in human malignancies," *Lab. Invest.* 82: 1755-1764, 2002.
International Search Report and Written Opinion in International Application No. PCT/US2013/072857 mailed on Feb. 21, 2014.
International Preliminary Report on Patentability in International Application No. PCT/US2013/072857 mailed on Jun. 18, 2015.

\* cited by examiner (c) HSC3 Cells with 60μM CPZ 24 hours (d) HSC3 Cells with 90μM CPZ 24 hours

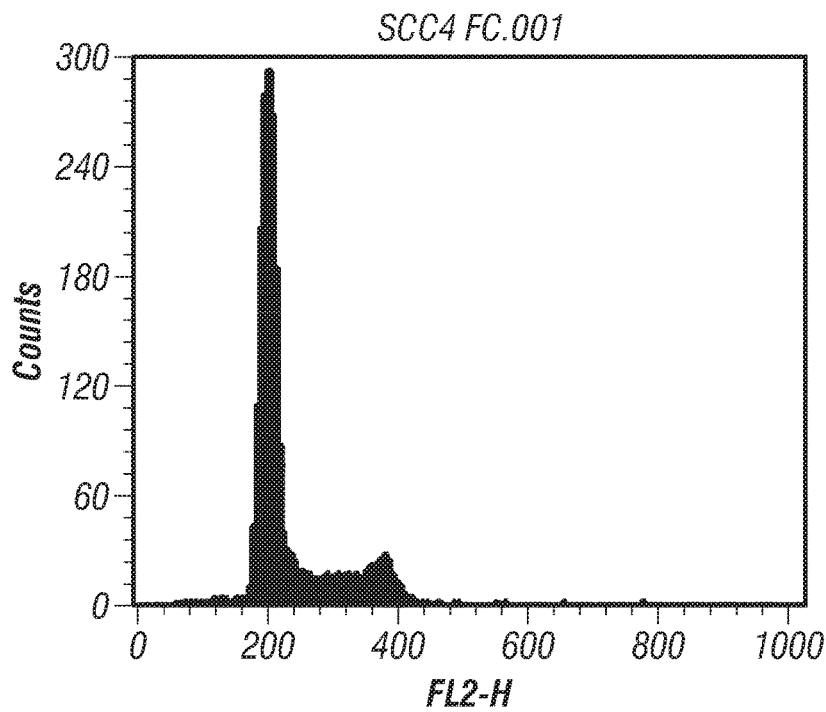
(a) SCC4 Cells with 0μM CPZ 24 hours
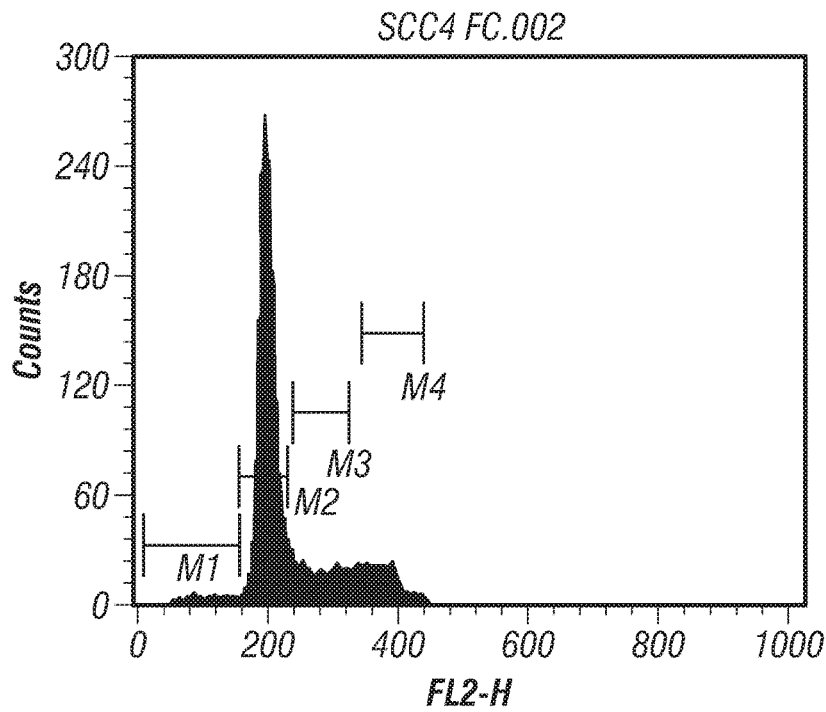
(b) SCC4 Cells with 30μM CPZ 24 hours
FIG. 1G-2

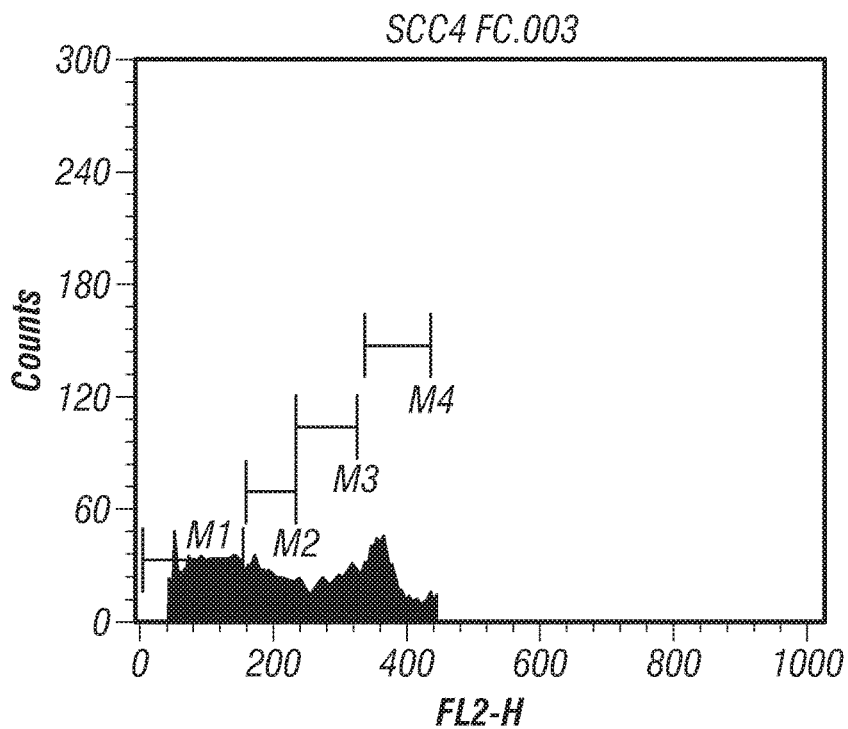
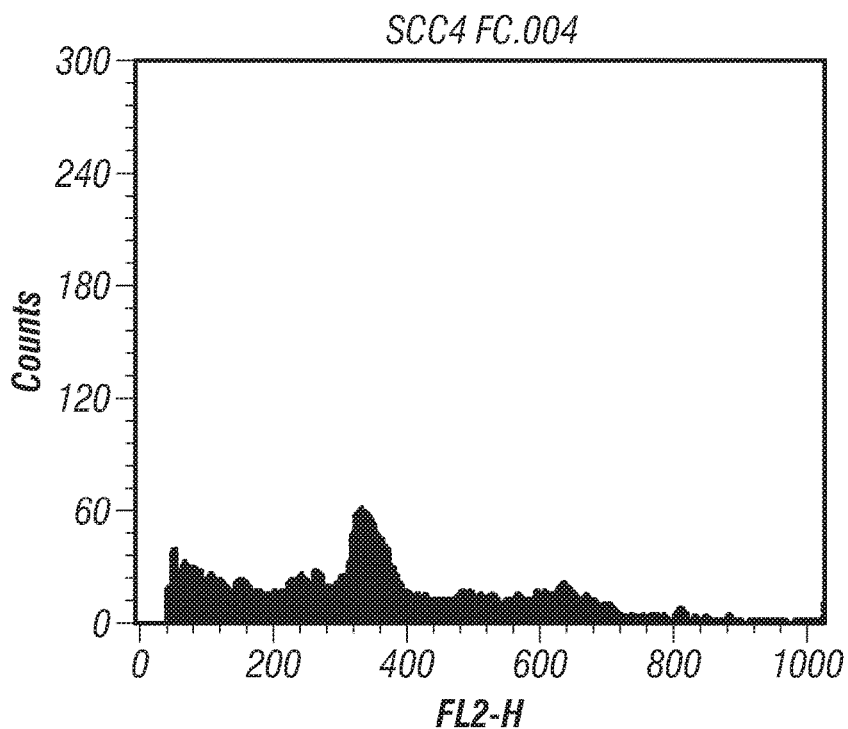
FIG. 1G-2 (Cont'd)

(a) SCC25 Cells with 0μM CPZ 24 hours
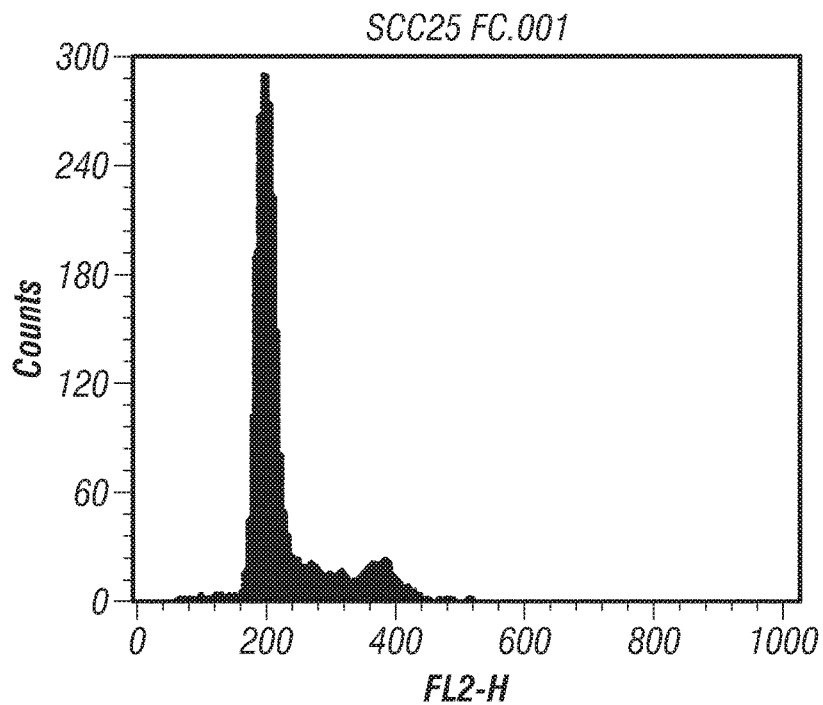
(b) SCC25 Cells with 30μM CPZ 24 hours
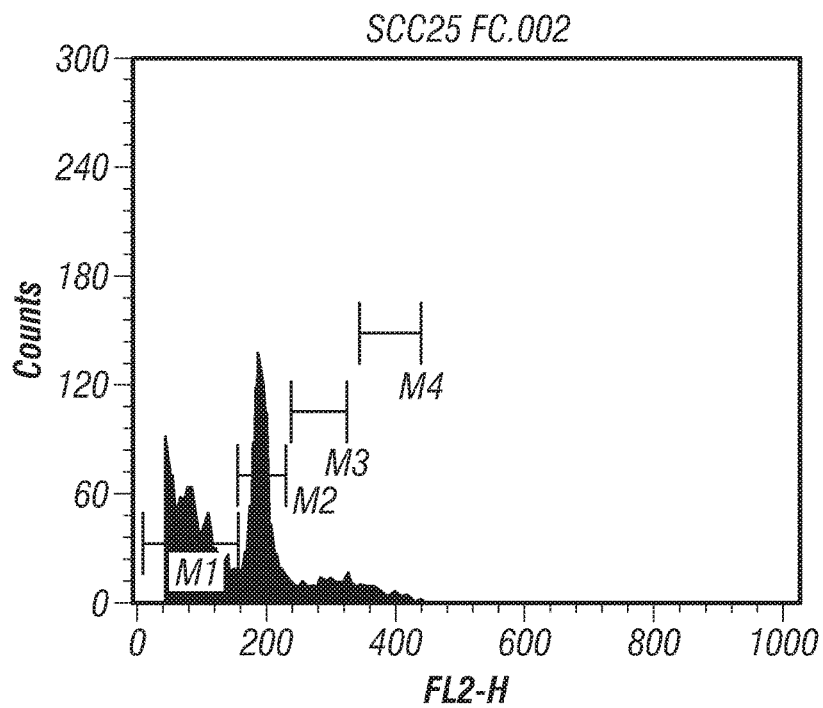
FIG. 1G-3

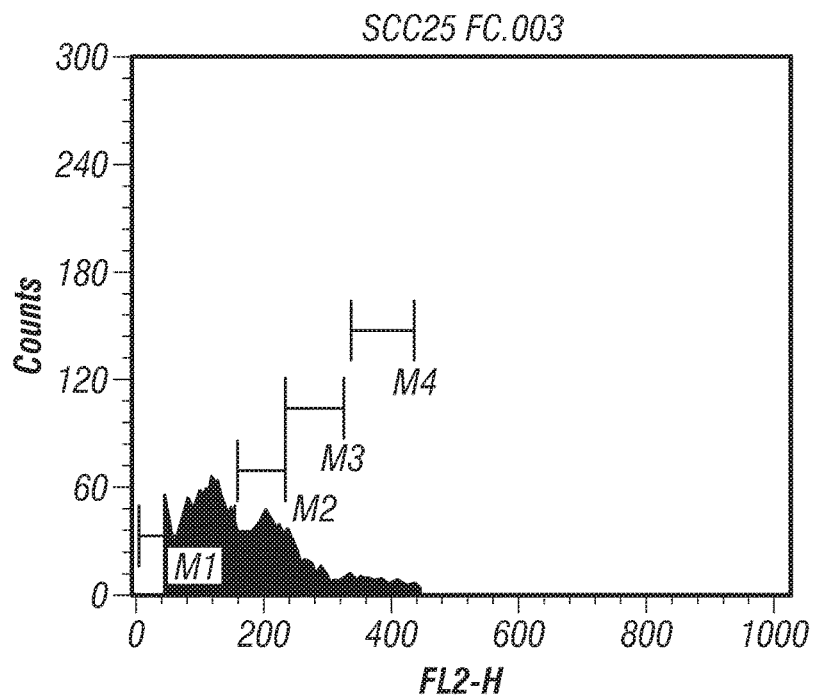
(c) SCC25 Cells with 60μM CPZ 24 hours
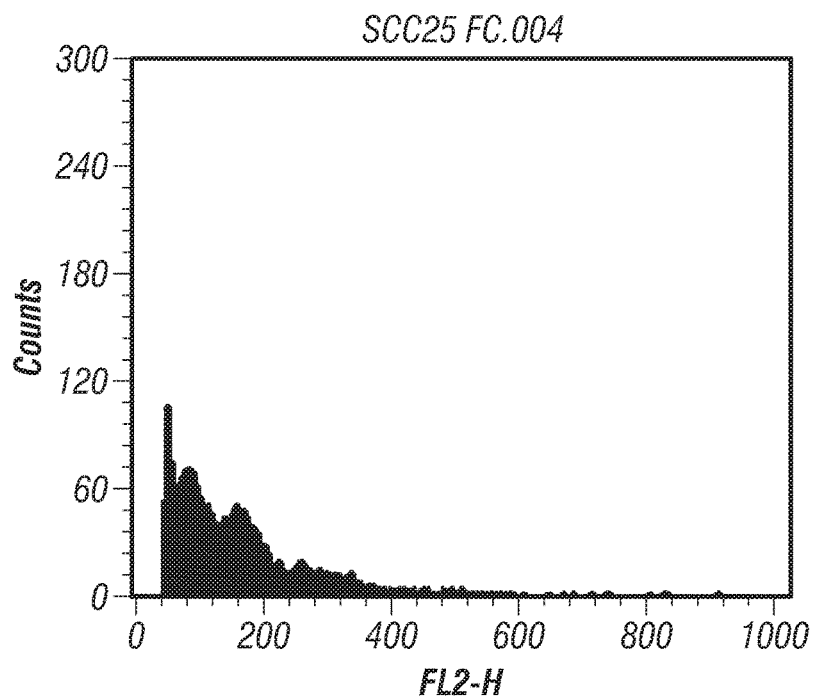
(d) SCC25 Cells with 90μM CPZ 24 hours
FIG. 1G-3 (Cont'd)

HSC3

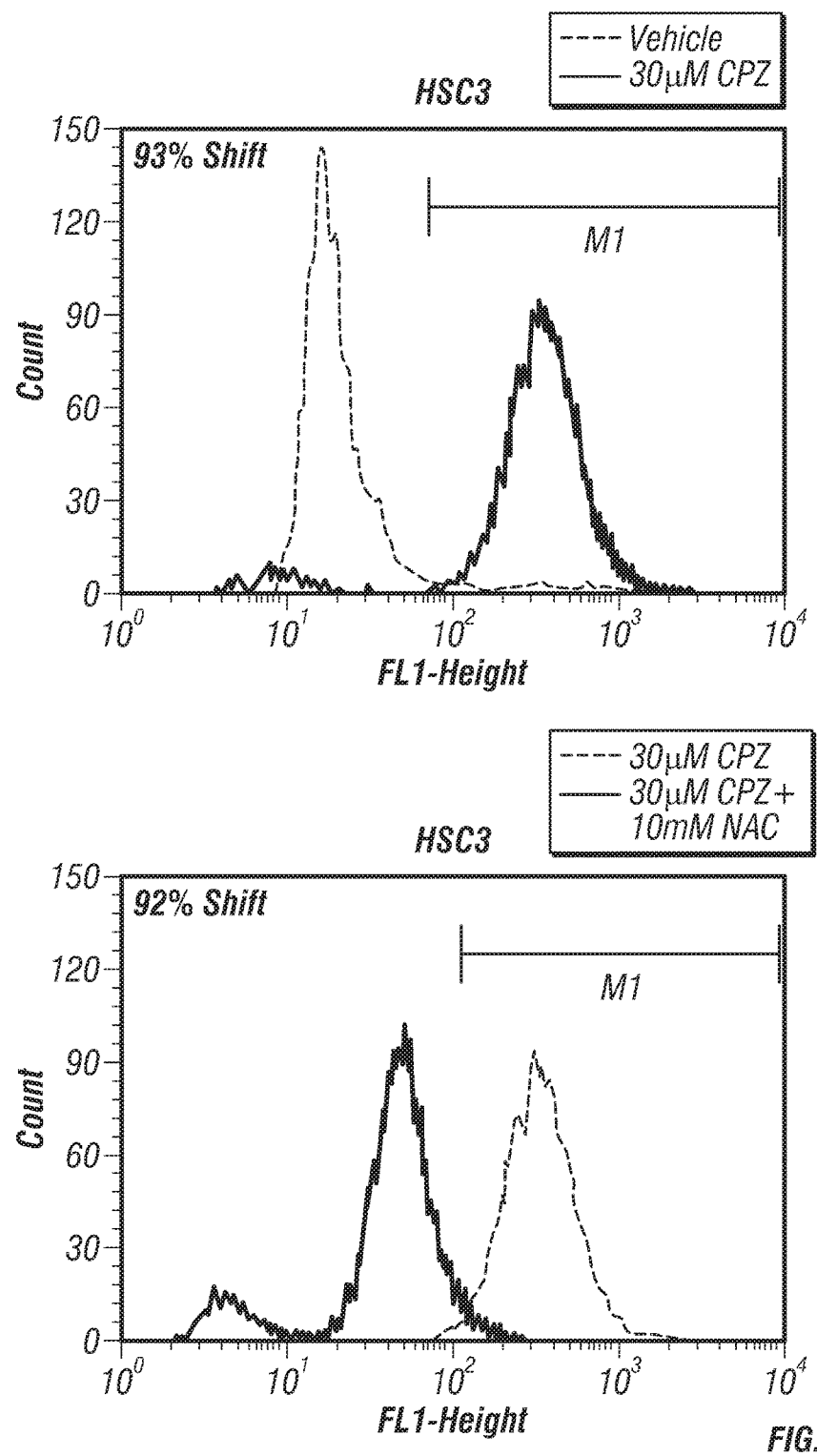
FIG. 1I-4(a)-(b)

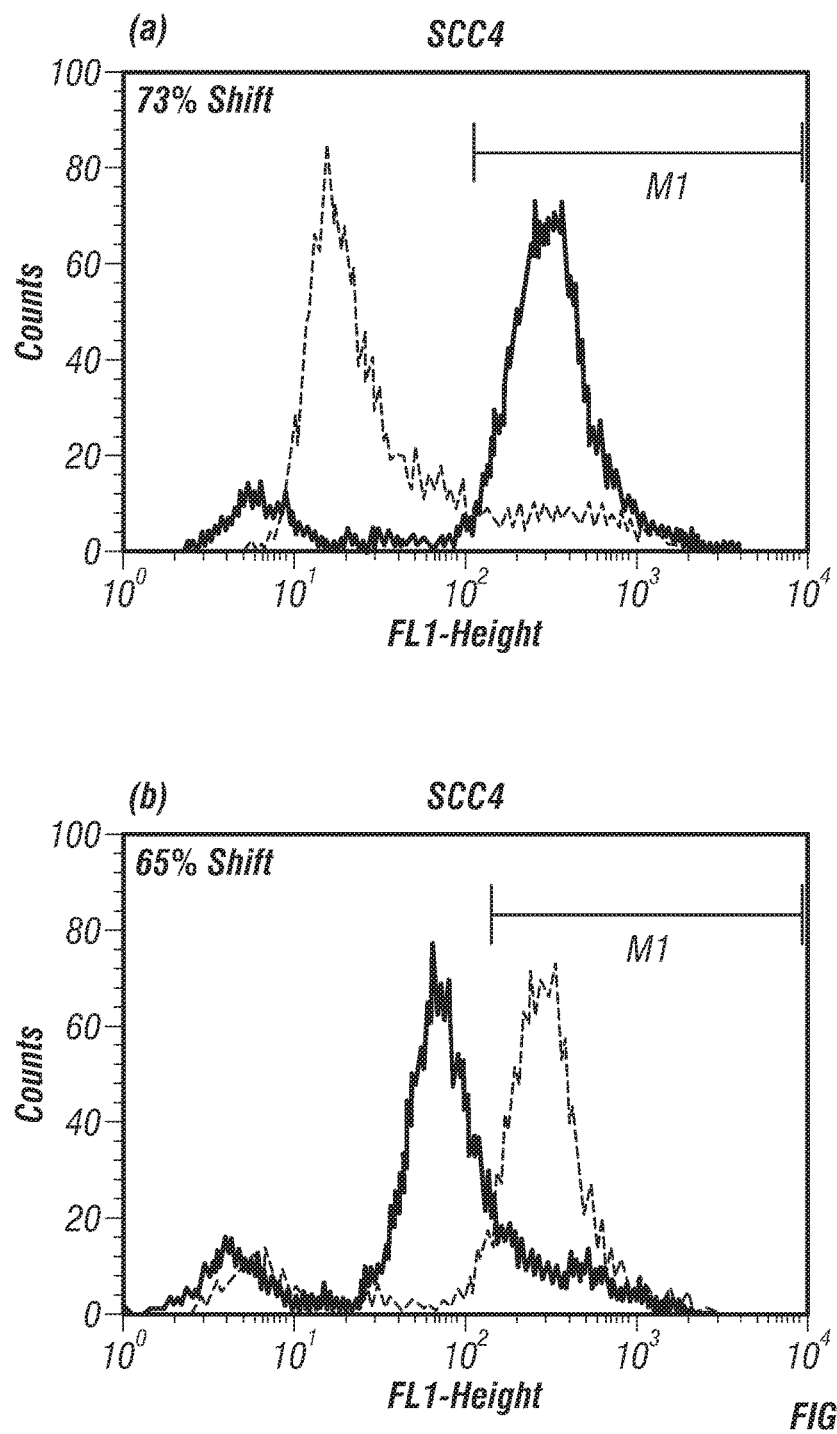
FIG. 1I-5(a)-(b)

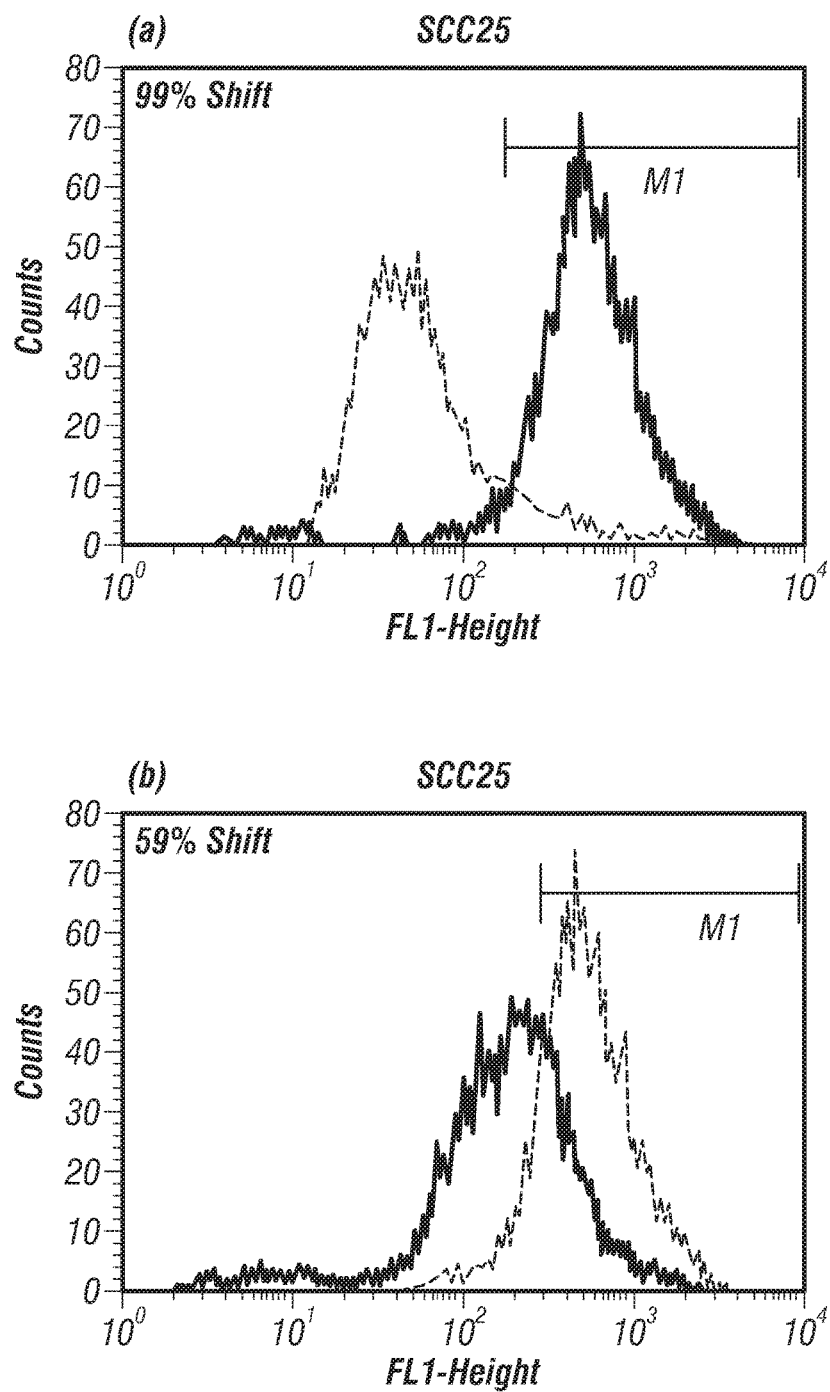
FIG. 1I-6(a)-(b)

HSC3 7% DMSO Vehicle Control

Liver and Kidney Function Tests

| Treatment | AST IU/L (r.v.=107.4 ± 41.9) | ALT IU/L (r.v.= 24.8 ± 10.1) | CREA MG/DL (r.v.= 0.2 ± 0.1) | BUN MG/DL (r.v.= 17.1 ± 3.7) | Liver/body weight (g/100g) | Kidney/body weight (g/100g) |
|---|---|---|---|---|---|---|
| Control | 137.4 + 59.38 | 47.59 + 15.68 | 0.0766 + 0.008 | 24.52 + 3.289 | 4.583 + 0.553 | 1.470 + 0.075 |
| CPZ | 101.3 + 35.95 | 35.14 + 8.013 | 0.0798 + 0.015 | 21.98 + 3.798 | 4.787 + 0.017 | 1.315 + 0.065 |

FIG. 14

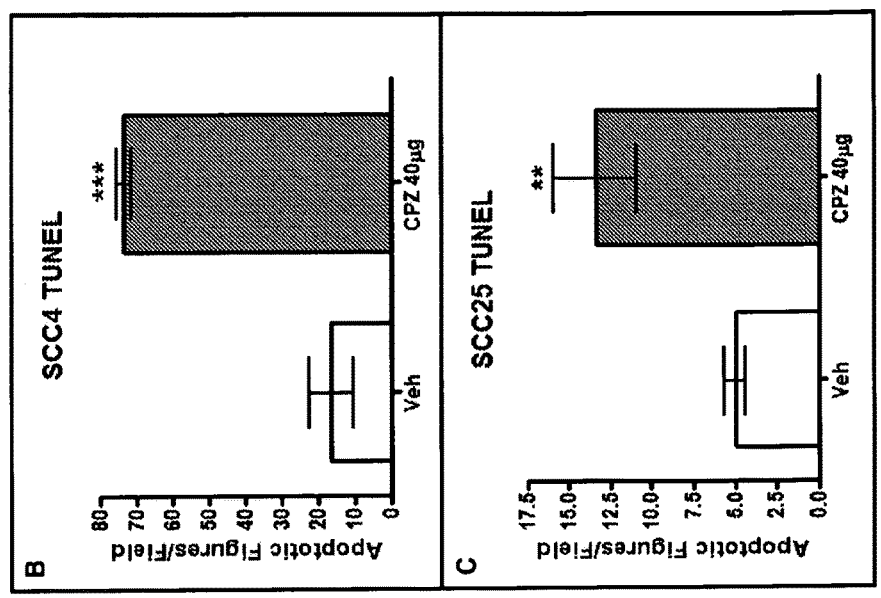
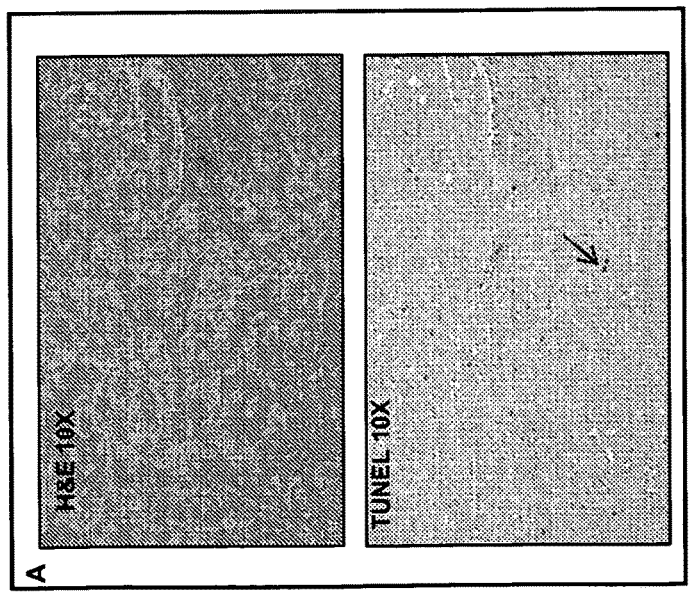
FIGS. 15A-C

USE OF CAPSAZEPINE AND ANALOGS THEREOF TO TREAT CANCER

CROSS REFERENCE TO RELATED APPLICATIONS

This application is a national phase application under 35 U.S.C. §371 of International Application No. PCT/US2013/072857, filed Dec. 3, 2013, which claims the benefit of priority of U.S. Provisional Patent Application No. 61/732,511, filed Dec. 3, 2012. The entire contents of each of the above-referenced disclosures are hereby incorporated by reference.

BACKGROUND OF THE INVENTION

A. Field of the Invention

The invention relates to methods and compositions for treating cancer, particularly solid tumor cancers. Methods and compositions include capsazepine (CPZ), that is, 2-[2-(4-chlorphenyl)ethylamino-thiocarbonyl]-7,8-dihydroxy-2,3,4,5-tetrahydro-1H-2-benzazepine, CPZ analogs, or other antagonists of TRP (transient receptor potential) channel Vanilloid subtype 1 (TRPV1, also known as "transient receptor potential cation channel, subfamily V, member 1").

B. Description of Related Art

CPZ has been characterized as a competitive antagonist of both capsaicin (CAP) and the CAP-related compound resiniferatoxin (RTX) [Bevan S., Hothi S. et al. (1992; "Capsazepine: a competitive antagonist of the sensory neurone excitant capsaicin," *Br. J. Pharmacol.* 107: 544-552)]. CAP and RTX are TRPV1 agonists, but CPZ blocks the activation by chemicals of the TRPV1 channel. In mammals, the TRPV1 channel functions as a pain and temperature sensor.

Numerous patent documents disclose CAP derivatives and their use in treating pain. For example, U.S. Pat. No. 5,403,868 ["Capsaicin derivatives"] discloses compounds having "in particular analgesic and anti-inflammatory" utility. Similarly, published U.S. Patent Publication No. 20060035939 ["3-aminobenzamide compounds and inhibitors of vanilloid receptor subtype 1 (VR1) activity"] and U.S. Pat. No. 7,906,508 ["3,4-dihydrobenzoxazine compounds and inhibitors of vanilloid receptor subtype 1 (VR1) activity"] disclose "treating diseases involved in VR1 activity such as pain, acute pain, chronic pain, neuropathic pain, rheumatoid arthritis pain, and neuralgia." Also, U.S. Pat. No. 7,514,562 ["Urea derivatives and their use as vanilloid receptor antagonists in the treatment of pain"] discloses testing vanilloid receptor antagonists for countering paw hyperalgesia in guinea pig. As a further example, U.S. Pat. No. 8,008,292 ["Condensed benzamide compounds and inhibitors of vanilloid receptor subtype 1 (VR1) activity"] discloses multiple compounds that alleviate pain and that resemble known vanilloid receptor subtype 1 (VR1) antagonist. Each patent document or other reference noted in this application is herein incorporated by reference in its entirety.

To various degrees, many of the compounds disclosed in these patent documents structurally resemble CPZ, the structure of which may be diagrammed as follows:

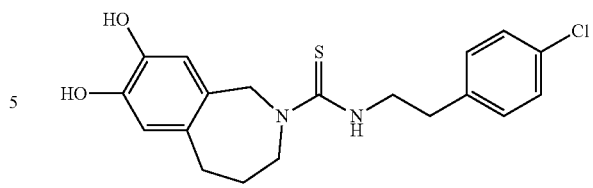

The disclosure herein relates to composition comprising CPZ or an analog of CPZ, and, in particular, the disclosure herein relates to the novel and nonobvious use of a composition comprising CPZ or an analog of CPZ in treating cancerous cell growth, particularly of a solid tumor cancer, in a subject.

Different types of solid tumors are named for the types of cells that form these tumors. Examples of types of solid tumor cancers include lymphomas (formed from lymphocytes), sarcomas (formed from cells of mesenchymal origin such as bone, cartilage, or muscle), and carcinomas (formed from cells of epithelial origin such as breast, colon, or lung).

Oral squamous cell carcinoma (OSCC) is the eighth most common cancer in the United States. Furthermore, OSCC is an extremely aggressive cancer that kills 50% of patients within five years of their initial diagnosis. While advances in local regional control have improved the overall survival for early disease stages 1 and 2, the death rate has not improved significantly in 40 years (American Cancer Society, Cancer Facts and Figures 2012). This is due primarily to the development of local recurrences and metastatic expansion that impinges upon critical structures thereby disallowing surgical resection. Importantly, as tumor burden increases and surgical resection is not possible, OSCC patients suffer immeasurable pain. Therefore, there is a great need to develop a means of reducing tumor volume to allow for either surgical resection or a prolonging of life expectancy for this patient population, or to assist in palliative care—both during treatment and for patients at the end of life.

TRP channels have been well-characterized in neurons where their functions are defined by induction of nociception in response to a noxious stimulus. However their expression and function in non-neuronal tissues, particularly in the context of malignant transformation, yet remain not well understood. Several authors have reported changes in expression of TRP channels in multiple tumor types (Prevarskaya, et al., 2007). TRPM1 has decreased expression in melanoma (Duncan, et al., 1998; Fang & Setaluri, 2000; Deeds, et al., 2000; Duncan, et al., 2001); TRPM8 has increased expression in prostate, breast, lung, colon, pancreatic cancers and melanoma (Tsavaler, et al., 2001; Fuessel, et al., 2003; Prevarskaya, et al., 2007; Mergler, et al., 2007); TRPV1 shows increased expression in prostate, colon and pancreatic cancers, but TRPV1 shows decreased expression as bladder cancer progresses (Domotor, et al., 2005; Hartel, et al., 2006; Lazzeri, et al., 2005; Sanchez, et al., 2005); and TRPV6 shows increased expression in prostate, breast, thyroid, colon, and ovarian cancers (Fixemer, et al., 2003; Zhuang, et al., 2002; Wissenbach, et al., 2004; Peng, et al., 2001; Peng, et al., 2000).

These findings have indicated that TRP channels might be useful as therapeutic targets for treating cancers. For example, it is hypothesized that treatment of tumors with TRP channel agonists, specific for tumor type, could result in a large influx of calcium (Ca++) thereby inducing apoptosis (Prevarskaya, et al., 2007). Reilly and colleagues demonstrated that treatment with the TRPV1 agonist CAP did result in apoptosis in cultured cells of an immortalized human bronchiolar epithelial cell line transformed with a TRPV1 insert to overexpress TRPV1 (Reilly, et al., 2003). However, a peculiar finding was seen in that the TRPV1 antagonist CPZ failed to reverse these effects. Curiously, CPZ appeared to be more effective at inducing apoptosis in these immortalized cultured cells than CAP (Reilly, et al., 2003). The authors conjectured that TRP channels often function in heteromeric tetramers with other TRP channels and perhaps this heteromeric interaction was not taking place within the cell lines tested.

Another separate study evaluated the effects of CAP on liver cancer cells. This study aimed to activate the TRPV1 channel and induce a high influx of calcium into the cells so as to trigger cell death (Reilly, et al., 2003). Investigators pretreated the cells with CPZ and noted that it failed to reverse the effects of CAP. The authors argued that TRPV1 also interacts with TRPA1 and conjectured that interaction with TRPA1 may be the reason why CPZ failed to reverse the effects of CAP. These and other studies again simply support the assessment that the expression and function of TRP channels like TRPV1 in non-neuronal tissues, particularly in the context of malignant transformation, yet remain not well understood.

COMMON ABBREVIATIONS

CAP: capsaicin
CPZ: capsazepine
DMEM: Dulbecco's modified Eagle's medium
DMSO: dimethylsulfoxide
FACS: fluorescence assisted cell sorting
NOK: normal oral keratinocytes
OSCC: oral squamous cell carcinoma
PARP: poly (ADP-ribose) polymerase
Q-PCR: quantitative polymerase chain reaction
ROS: reactive oxygen species
TRP: transient receptor potential
TRPA1: transient receptor potential cation channel, subfamily A, member 1
TRPM1: transient receptor potential cation channel, subfamily M, member 1
TRPM8: transient receptor potential cation channel, subfamily V, member 8
TRPV1: transient receptor potential cation channel, subfamily V, member 1
TRPV6: transient receptor potential cation channel, subfamily V, member 6

SUMMARY OF THE INVENTION

The inventor is believed to be the first to have investigated expression of TRPV1 in oral cancer cell lines. The inventor is believed also to be the first to have used the TRPV1 antagonist CPZ to treat tumor growth, as well as to deliver CPZ by local injection directly into accessible tumors for treatment of tumor growth.

The inventor has discovered that CPZ is surprisingly effective in halting OSCC tumor cell proliferation in vitro and in vivo, but that the mechanism of action for the anti-proliferative activity of CPZ is generally independent of TRPV1 interactions. This mechanism of action is quite unexpected for a TRPV1 antagonist like CPZ. The inventor has shown that the anti-proliferative activity of CPZ works at least in part through inhibiting the electron transport system, which results in the generation of reactive oxygen species (ROS) and cell death. The inventor has further shown that solid tumors, such as OSCC tumors, can be directly accessed and effectively treated with local injections of CPZ. Studies on cultured cell lines support the view that the same results may be obtained through the use of CPZ (and its analogs) on other solid tumor cancers, including prostate cancer and primary breast cancer that has not metastasized.

The inventor has additionally discovered several particularly exciting advantages to the use of CPZ to treat solid tumor cancers, including: an absence of toxicity for liver and kidney functions, as well as straightforward means both to manage pain and to circumvent the need for intravenous injections while reversing tumor growth. Reduction in tumor volume and blockage of pain-inducing TRPV1 channels, even if not ultimately curative, promises to provide a better quality of life and may prove particularly useful in palliative care. In addition, direct, intra-tumoral injection of CPZ or a CPZ analog (possibly another TRPV1 antagonist) as presented by the inventor, offers the advantage of avoiding pronounced hyperthermia or pronounced hypothermia. In particular, TRPV1 is thought to have a key role in detection and regulation of body temperature, and hyperthermia is commonly associated with administration TRPV1 antagonists for systemic distribution. Directly injecting CPZ (or a CPZ analog) intra-tumorally avoids inducing particularly the pronounced hyperthermia that may accompany administering TRPV1 antagonists for systemic distribution.

Notwithstanding the pronounced hyperthermia that has been reported in studies involving administration of some TRPV1 antagonists for systemic distribution, some embodiments of this invention include systemic administration. Studies involving intravenous administration of CPZ for analgesic use (Garami et al, 2010) demonstrated that, unlike other TRPV1 antagonists, CPZ does not cause hyperthermia in a rat model at a high intravenous administration dose. Furthermore, cell viability assays conducted by the inventor demonstrate that CPZ induces cell death in cancer cell lines but does not induce death of normal, non-malignant oral keratinocytes. No inflammation, ulceration, necrosis or pain were evident in adjacent healthy tissues in tumor bearing mice treated by intratumoral injection with CPZ. Liver and kidney function tests of tumor bearing mice treated by intratumoral injection with CPZ did not demonstrate negative effects on liver or kidney function. Use of CPZ (and its analogs) by systemic administration may allow treatment of metastatic cancers and primary cancers that are not readily accessible for direct injection.

In one instance, there is disclosed a method for reducing cancerous tumor cell growth, the method comprising administering an effective amount of a composition comprising CPZ or an analog of CPZ to a subject having or suspected of having cancerous tumor cell growth. According to one aspect, the subject has been diagnosed with a cancerous solid tumor. According to another aspect, the composition comprising CPZ or an analog of CPZ is administered by injection intra-tumorally. Alternatively, in related aspects, the composition comprising CPZ or an analog of CPZ is administered for distribution systemically within the subject.

According to some embodiments, the effective amount of a composition comprising CPZ or an analog of CPZ that is administered in a method for reducing cancerous tumor cell growth in a subject having or suspected of having cancerous tumor cell growth further comprises a pharmaceutically acceptable carrier or diluent, which, according to one aspect, may comprise a saline solution combined with a solvent to assist in the dissolution of CPZ or an analogue thereof. In various embodiments, the solvent can include dimethyl sulfoxide (DMSO), polysorbate (e.g., polysorbate 80), N-methyl pyrrolidone (NMP), polyethylene glycol (e.g., PEG 300), polyethoxylated castor oil (e.g., Kollphor EL®), ethanol, or a combination thereof. For example, the composition can comprise 0.1% to 10% polysorbate; 0.1% to 10% ethanol; 0.1% to 20% NMP; 0.1% to 10% polyethoxylated castor oil; and/or 0.1% to 100% PEG combined with saline solution to bring to the appropriate concentration.

In another aspect, the composition comprising CPZ or an analog of CPZ that is administered to a subject having or suspected of having cancerous tumor cell growth comprises a second active agent. According to a related aspect, the second active agent comprises inhibitors of coenzyme Q, such as CAP, statin drugs, beta-blockers or blood sugar lowering drugs.

According to some embodiments, the composition comprising CPZ or an analog of CPZ may be administered at the same time as the composition comprising a second active agent. Alternatively, the composition comprising CPZ or an analog of CPZ may be administered before the composition comprising a second active agent is administered, or the composition comprising CPZ or an analog of CPZ may be administered after the composition comprising a second active agent is administered. For example, the interval of time between administration of a composition comprising CPZ or an analog of CPZ and a composition comprising a second active agent may be 1 to 30 days, or it may be 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more, or any integer derivable therein, hours or days.

According to further embodiments, the composition comprising CPZ or an analog of CPZ that is administered for reducing cancerous tumor cell growth to a subject having or suspected of having cancerous tumor cell growth is taken from a preparation comprising a pharmaceutically acceptable carrier. In related aspects, the preparation meets pharmacopeial requirements for sterility, pyrogens, and particulate matter or other contaminants. In further related aspects, the preparation is formulated for intratumoral injection. Alternatively, in related aspects, the preparation is formulated for distribution systemically within the subject. In one aspect of disclosed embodiments, the subject of the method for reducing cancerous tumor cell growth is a mammal. In related aspects, the subject is a human.

According to further related embodiments, the subject having or suspected of having cancerous tumor cell growth and to whom an effective amount of a composition comprising CPZ or an analog of CPZ is administered, has oral squamous cell carcinoma, head and neck cancer, breast cancer, cervical cancer, or prostate cancer. Such administration can be systemic or local. According to various embodiments, the cancer has not metastasized. However, in other embodiments, the cancer has metastasized.

According to further related embodiments, the subject having or suspected of having cancerous tumor cell growth and to whom an effective amount of a composition comprising CPZ or an analog of CPZ is administered, is experiencing pain associated with the cancerous tumor cell growth. In some related aspects, TRPV1 channels in pain-sensing neurons are expressed in the subject, which, in related instances, may be in the head and neck. Similarly, the composition comprising CPZ or an analog of CPZ that is administered for reducing cancerous tumor cell growth to a subject having or suspected of having cancerous tumor cell growth, blocks inferior alveolar nerve signals in the subject.

In this way, or in other ways, the composition comprising CPZ or an analog of CPZ may in related aspects alleviate pain in the subject. In further related aspects, the composition comprising CPZ or an analog of CPZ simultaneously alleviates pain and reduces cancerous tumor cell growth in the subject.

According to some embodiments, the composition comprising CPZ or an analog of CPZ that is administered in a method for reducing cancerous tumor cell growth in a subject having or suspected of having cancerous tumor cell growth inhibits cancerous tumor cell growth in the subject. In related aspects, the composition reduces cancerous tumor cell growth in the subject, and, in further related aspects, cancerous tumor cell growth is reduced in a cancerous solid tumor in the subject. In some aspects, inhibition of cancerous tumor cell growth in the subject may allow for extension or prolongation of life. In some aspects, reduction in cancerous tumor cell growth in the subject makes an inoperable tumor into an operable tumor through shrinkage of the tumor. In further related aspects, the composition comprising CPZ or an analog of CPZ reduces cancerous tumor cell growth in the subject in a TRPV1 independent manner. In additionally further related aspects, the composition comprising CPZ or an analog of CPZ is administered to a subject having or suspected of having cancerous tumor cell growth without inducing either pronounced hypothermia or pronounced hyperthermia in the subject. In certain instances, administering an effective amount of a composition comprising CPZ or an analog of CPZ to a subject having or suspected of having cancerous tumor cell growth is as palliative care to the subject.

In the disclosed methods, the composition comprising CPZ or an analog of CPZ may be delivered in any suitable manner. In various embodiments, the composition comprising CPZ or an analog of CPZ is administered locally, such as by injection intratumorally. In another aspect, the composition comprising CPZ or an analog of CPZ may be systemically administered. For example, the composition comprising CPZ is orally or intravenously administered to the subject.

Unless otherwise specified, the percent values expressed herein are weight by weight and are in relation to the total composition.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting," "reducing," "treating," or any variation of these terms, includes any measurable decrease or complete inhibition to achieve a desired result, although "reducing" particularly may connote more than cessation in growth (e.g., in contrast to "inhibiting," which may, in some instances, be limited to cessation in growth). Similarly, the term "effective" means adequate to accomplish a desired, expected, or intended result.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps, in relation to the total composition.

The compositions and methods for their use can "comprise," "consist essentially of," or "consist of" any of the ingredients or steps disclosed throughout the specification. With respect to the transitional phase "consisting essentially of," in one non-limiting aspect, a basic and novel characteristic of the compositions and methods is the ability of CPZ (or an analog of CPZ) to treat solid tumor cancers.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1D-1. Cell viability assays reported as % of vehicle control (n=3). OSCC cell lines (HSC3, SCC4, and SCC25) were treated with CAP (30 μM), CAP (150 μM), CPZ (30 μM), and a combination of CAP (150 μM)/CPZ (30 μM) for 24 hours. VEH=delivery vehicle control without CAP or CPZ. *p<0.05, ***p<0.001. TRPV1 mRNA is expressed in OSCC cell lines (see FIG. 1A). Treatment with CAP induces OSCC cell death in SCC4 and SCC25 cell lines [CAP 150 μM]. However, addition of the TRPV1 antagonist CPZ (30 μM) does not reverse this effect, but furthers induction of cell death in all three cell lines [CAP 150 μM+CPZ 30 μM]. Furthermore, CPZ (30 μM) alone induces OSCC cell death in all three cell lines [CPZ 30 μM]. These results indicate that the "cell death" effects of CPZ, and possibly CAP, are independent of TRPV1 interactions.

FIG. 1D-2. Cell viability assays reported as % of vehicle control (n=3). Immortalized non-malignant oral keratinocytes OKF6 cells were treated with CAP (150 μM), CPZ (30 μM), and a combination of CAP (150 μM)/CPZ (30 μM) for 24 hours. VEH=delivery vehicle control without CAP or CPZ. *p<0.05, ***p<0.001. Treatment with high concentrations of CAP induces death of normal, non-malignant OKF6 cells. The effect of which was reversed by the pre-treatment with CPZ. This demonstrates that TRPV1 channels are functioning as expected in normal keratinocytes. This data also shows the non-toxic effect of CPZ on normal, non-malignant OKF6 cells.

FIGS. 1E-1, 1E-2, and 1E-3. Cells of HSC3 [FIG. 1E-1 (a)-(d)], SCC4 [FIG. 1E-2(a)-(d)], and SCC25 [FIG. 1E-3 (a)-(d)] cell lines, after being treated with CPZ for 24 hours, undergo apoptosis. In FIG. 1E-1, magnifications of (from left to right) vehicle control HSC3 cells (a) and HSC3 cells treated with 30 μM CPZ (b), 60 μM CP(c), or 90 μM CPZ(d). In FIG. 1E-2, magnifications of (from left to right) vehicle control SCC4 cells (a) and SCC4 cells treated with 30 μM CPZ (b), 60 μM CPZ (c), 90 μM CPZ (d), while, in FIG. 1E-3, magnifications of (from left to right) vehicle control SCC25 cells (a) and SCC25 cells treated with 30 μM CPZ (b), 60 μM CPZ (c), or 90 μM CPZ (d).

FIGS. 1G-1 to 1G-3. Flow sort data shown. Flow sort diagrams for HSC3 [FIG. 1G-1], SCC4 [FIG. 1G-2], and SCC25 [FIG. 1G-3] cells after 24 hours treatment (by quadrant) with 0 μM (a), 30 μM (b), 60 μM (c), and 90 μM (d) CPZ—as further detailed in data of Table 1. The scale of the y-axis for all diagrams is 0 to 300 counts.

FIGS. 1H-1 to 1H-3. FIG. 1H-1: Cell viability assays of OSCC cell lines treated with 30 μM CPZ alone or in combination with 10 mM N-Acetyl-L-Cysteine (NAC) for 24 h (n=4); ***p<0.001. FIG. 1H-2: Cell viability assay of MDA231 cells treated with CPZ for 24 h with and without NAC. FIG. 1H-3: Cell viability assay of PC3 cells treated with CPZ for 24 h with and without NAC. Capsazepine induces a significant dose dependent cytotoxicity in OSCC cell lines, MDA231 breast cancer cells, and PC3 prostate cancer cells. This effect is reversed by the addition of 10 mM NAC.

FIGS. 1I-1 to 1I-3. Reactive oxygen species (ROS) assays. The level of ROS in OSCC cell lines was examined by flow cytometry using 2,7-dichlorodihydrofluorescein diacetate (DCFH-DA; Sigma). Approximately $3 \times 10^5$ cells were plated in 12-well plates. To detect ROS, cells were incubated for 30 min at 37° C. with DCF-DA, washed and then treated for 1 h with 30 μM capsazepine (grey, thick line), 150 μM capsaicin (grey, thin line), 30 μM capsazepine+150 μM capsaicin (black line), or vehicle control (dotted line). The cells were harvested, washed twice, and analyzed by flow cytometry. Cells treated with capsazepine and/or capsaicin demonstrate a shift in their peaks to the right of control cells (dotted line). This shift is indicative of an increase in ROS.

FIGS. 1I-4(a)-(b) to 1I-6(a)-(b). Induction of ROS in OSCC cell lines. (a). ROS induction in OSCC cell lines following 1 h treatment with 30 μM CPZ (black line) compared to vehicle control. (b). ROS induction in OSCC cell lines following 1 h treatment with 30 μM CPZ is reversed by NAC co-treatment (black line) as indicated in the shift in their peaks to the left.

FIGS. 1J-1 to 1J-2. FIGS. 1J-1(a) to (c): Calcium imaging of OSCC cell lines (HSC3, SCC4, and SCC25) treated with 20 μM capsaicin (CAP) alone or in combination with 10 μM capsazepine (CPZ) or treated with 3 μM ionomycin positive control (n=3). FIGS. 1J-2(a) to (c): Calcium imaging of OSCC cell lines (HSC3, SCC4, and SCC25) treated with cytotoxic doses of CAP (150 μM) alone or in combination with cytotoxic dose of CPZ (30 μM) or treated with 3 μM ionomycin positive control (n=3). Arrow indicates time point when treatment was added. This calcium imaging data reveals that TRPV1 channels are not functional in these OSCC cell lines. Capsaicin fails to cause an influx of calcium at 20 μM concentrations. CAP concentrations at the cytotoxic level (150 μM capsaicin) revealed calcium outflow occurred over a prolonged period of time. This was due to the toxic effects of this high capsaicin concentration which permeablized the cell membrane allowing calcium to flow freely out of the cell. This was not reversed by capsazepine. Instead, capsazepine at cytotoxic dose (30 μM) had no effect on intra-cellular calcium levels. These finding confirm that activation of TRPV1 is not the mechanism by which cell death is induced using capsazepine.

FIG. 2A. TRPV1 Knock-down in HSC3 cells. Cell proliferation assays of HSC3 cells transfected with TRPV1 siRNA and treated with: 150 μM CAP [CAP 150 μM]; 30 μM CPZ [CPZ 30 μM]; or 150 μM CAP plus 30 μM CPZ [CAP 150 μM+CPZ 30 μM]. VEH=delivery vehicle control without CAP or CPZ. ***p<0.001.

FIG. 4. HSC3 xenografts. Tumor growth (% change) over time. Veh=delivery vehicle control without CPZ; CPZ 40 μg=40 μg CPZ in 40 μl Veh medium (1 μg/μl) injected directly into the tumor every other day. *p<0.05, **p<0.01.

FIG. 5. HSC3 xenografts. Overall tumor growth after 12 days (% change). Veh=delivery vehicle control without CPZ; CPZ 40 μg=40 μg CPZ in 40 μl Veh medium (1 μg/μl). ** p<0.01.

FIG. 6. Panels A & B: HSC3 xenografts treated with 7% DMSO vehicle control (arrows).

FIG. 14. Liver and kidney function tests of tumor bearing mice following two week treatment with either vehicle control (Control) or 40 μg CPZ in 40 μl Veh medium (1 μg/μl) injected directly into tumor every other day over 14 days (CPZ). No negative effects on liver or kidney function were detected.

FIG. 15A-15C. TUNEL staining of OSCC xenografts. FIG. 15A: Representative photomicrograph of TUNEL stain of HSC3 xenograft (10×) treated with vehicle control. Arrow demonstrates apoptotic figure. FIG. 15B: Number of apoptotic figures per field in vehicle and 40 μg capsazepine (CPZ) treated SCC4 xenografts. FIG. 15C: Number of apoptotic figures per field in vehicle and CPZ (20 m) treated SCC25 xenografts. Student's T-Test of the average of six fields with n=3; ***p<0.001.

DESCRIPTION OF ILLUSTRATIVE EMBODIMENTS

Figure 1A:
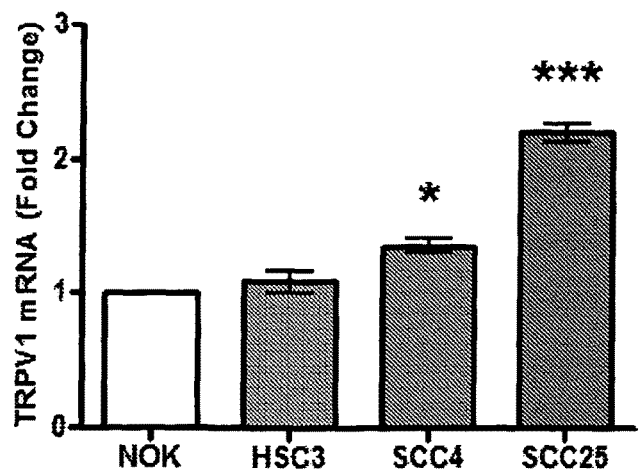
FIG. 1A. Quantitative PCR (Q-PCR) analysis of TRPV1 mRNA expression in three OSCC cell lines (HSC3, SCC4, and SCC25) relative to normal oral keratinocytes (NOK); *p<0.05, ***p<0.001.
Figure 1B:
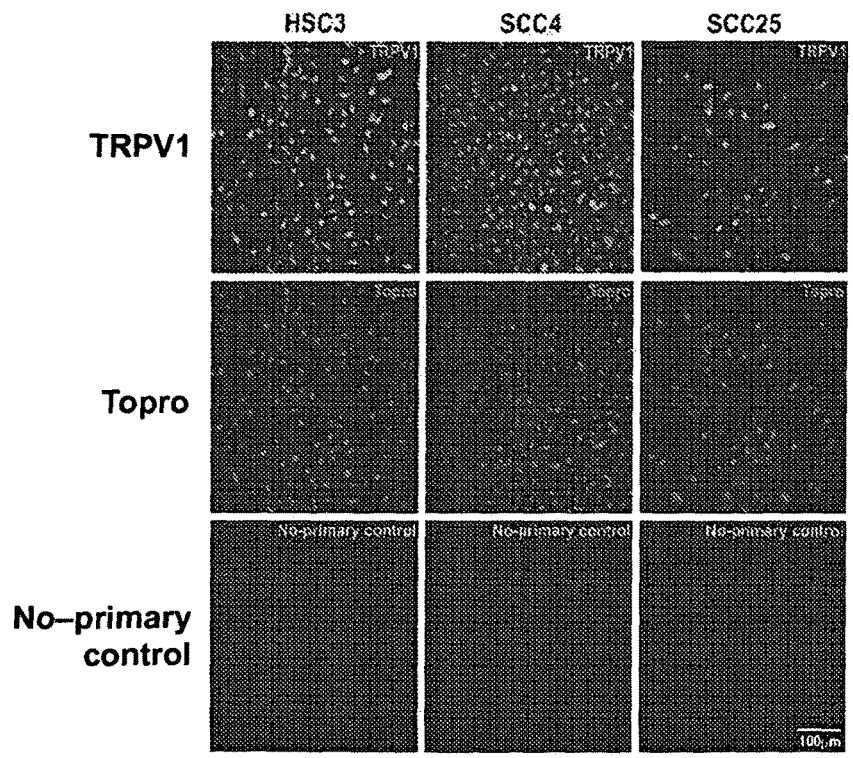
FIG. 1B. Confocal microscopy shows TRPV1 expression in OSCC cell lines: TRPV1—top row; TOPRO—middle row; and Primary Antibody Control (no staining observed)—bottom row.
Figure 1C:
FIG. 1C. Immunohistochemical staining of TRPV1 channels in normal oral mucosa and OSCC (4×): epithelium (E); connective tissue (C); and OSCC (outlined by box in image labeled OSCC-1).
Figures 1, 1D, 2:
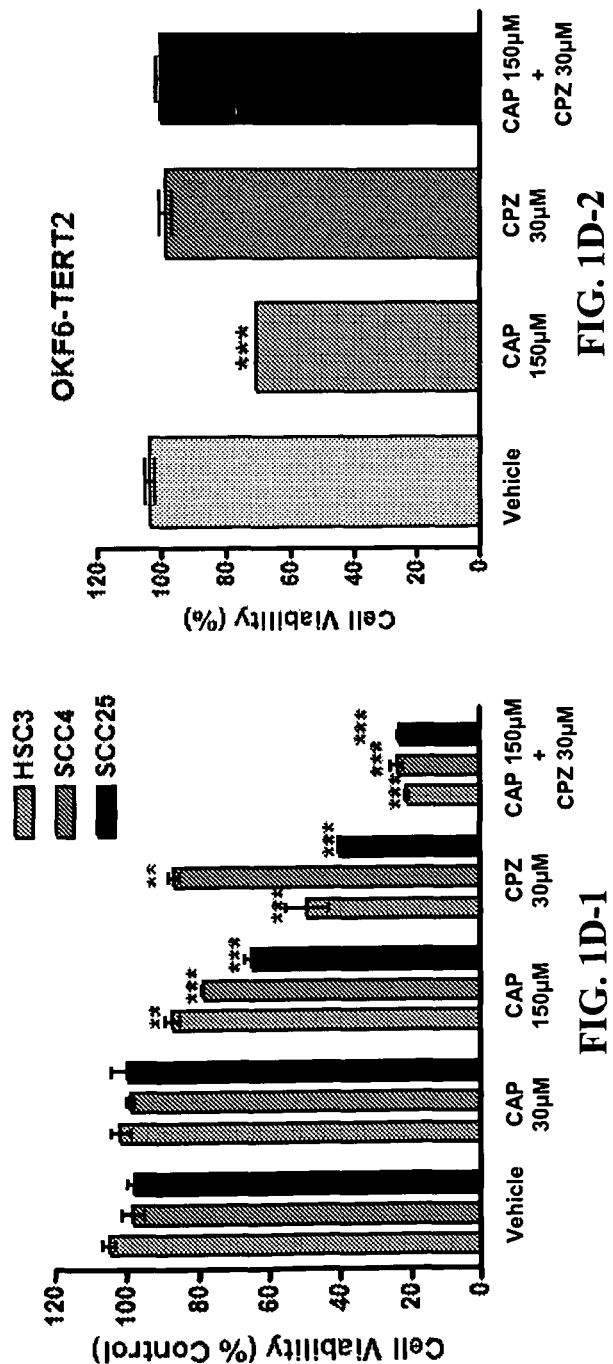
Figures 1, 1E, 2, 3:
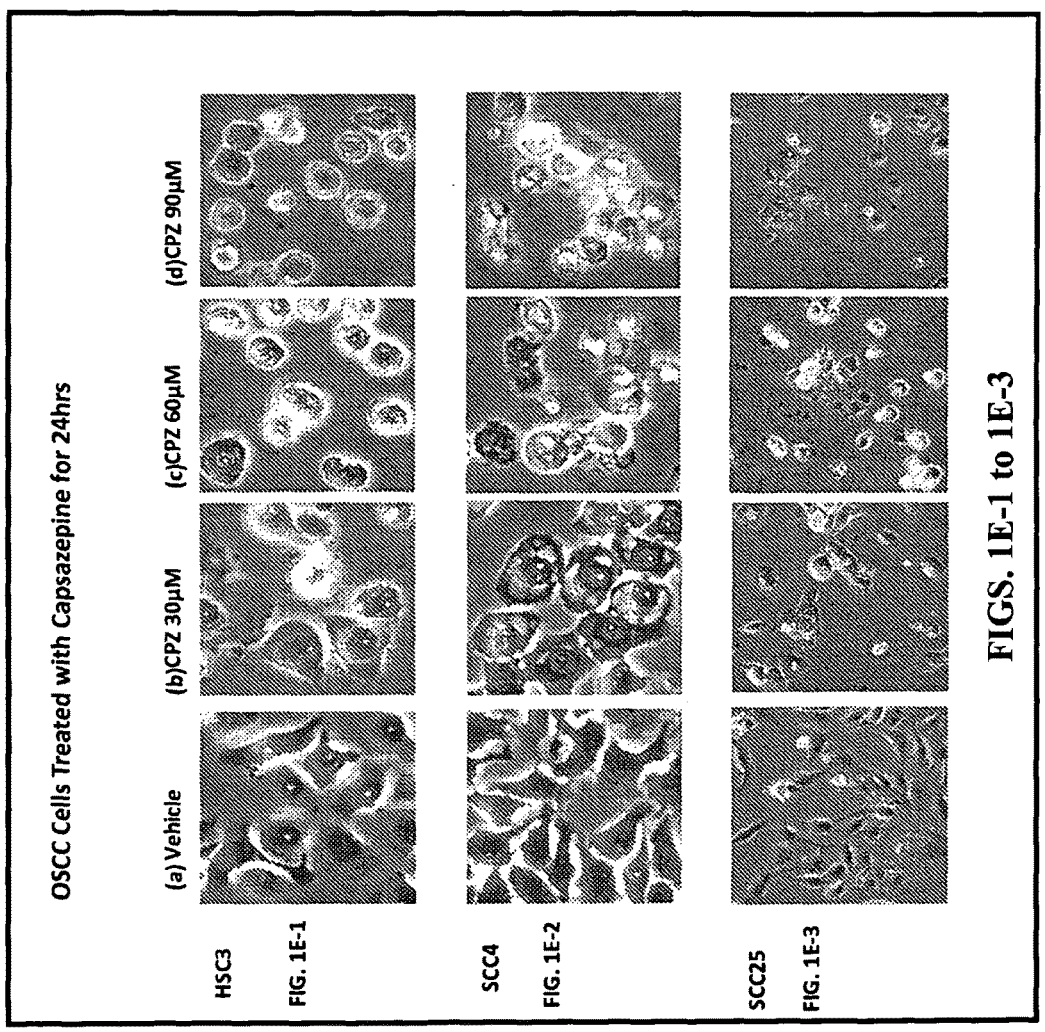

Preliminary studies of TRP channel expression in OSCC cell lines determined that the TRP channel Vanilloid subtype 1 (TRPV1) is over-expressed in OSCC (FIG. 1A; see also immunofluorescent staining [FIG. 1B] and immunohistochemical staining [FIG. 1C] of TRPV1 channels in OSCC cells lines). Dose-response curves followed by cell proliferation assays confirmed that capsaicin (CAP) significantly reduces cell viability (p<0.001) at relatively high concentrations (150 µM) in HSC3, SCC4 and SCC25 cell lines and that capsazepine (CPZ) failed to reverse these effects [FIG. 1D-1]. CPZ (30 µM) alone also significantly reduced cell viability and pre-treatment with CPZ followed by CAP had a dramatic additive effect resulting in 80% reduction of cell viability following 24 hrs of treatment. These findings were consistent in all OSCC cell lines tested (e.g., HSC3, SCC4, and SCC25 cell lines) (see FIG. 1D-1). Furthermore, equi-doses (30 µM) of CAP and CPZ demonstrate that CPZ has significant cytotoxic effects in all OSCC cell lines tested (HSC3, SCC4, and SCC25) at this low dose whereas CAP does not. [FIG. 1D-1].

By comparison, normal, non-malignant cells OKF6-Tert2 were treated with CAP causing a reduction in cell viability, but treatment with CPZ reversed the effects. (See FIG. 1D-2). Moreover, no toxicity was observed for CPZ.

A. Apoptosis Studies

To determine if reduced cell viability was due to apoptosis, flow-sort analysis and microscopic analysis of cells in three OSCC cell lines (HSC3, SCC4, and SCC25) following treatment were performed. When treated with CPZ for 24 hrs, cells from each of these cell lines undergo apoptosis. (Compare FIGS. 1E-1(b) to (d), FIGS. 1E-2(b)-(d), and FIGS. 1E-3(b) to (d) with FIG. 1E-1(a), FIG. 1E-2(a), and FIG. 1E-3(a), respectively.)

Figure 1F:
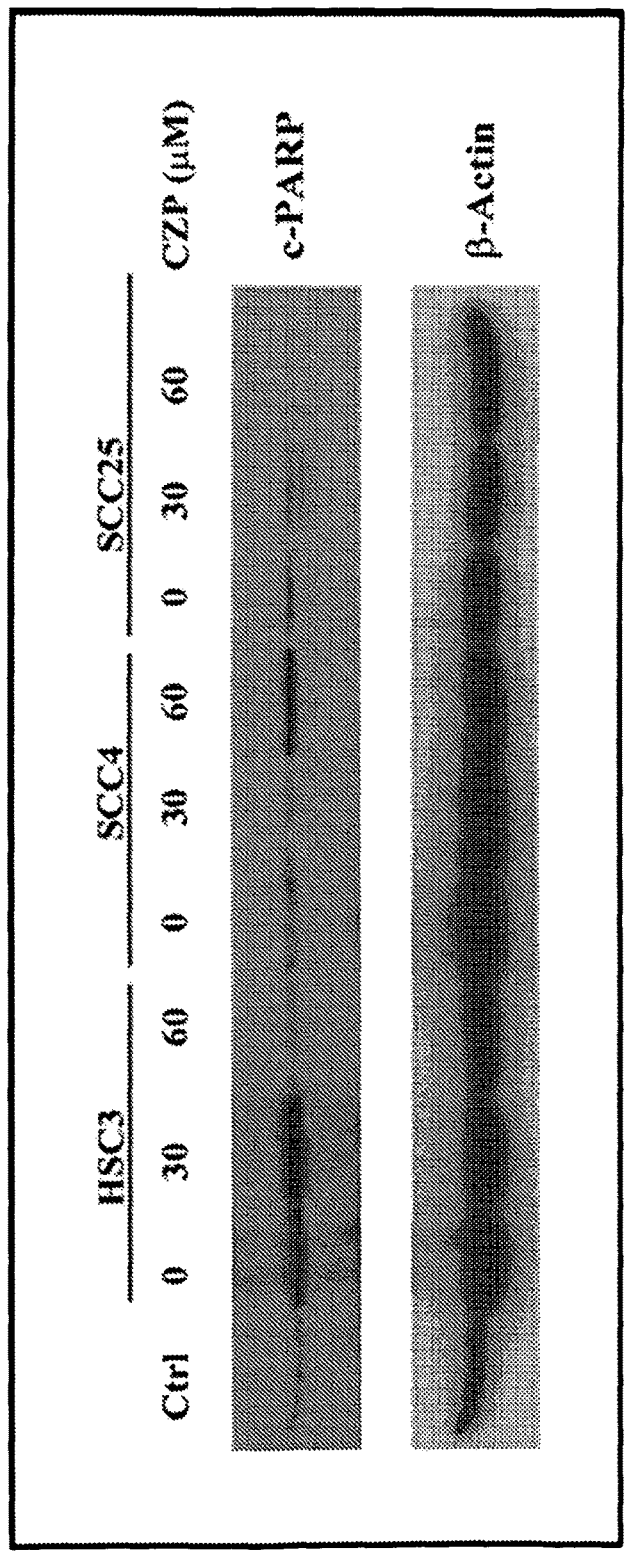
FIG. 1F. Western blot analysis demonstrating induction of cleaved PARP (c-PARP, a marker of apoptosis) in OSCC cell lines (HSC3, SCC4, and SCC25) treated with increasing doses of CPZ for 24 h. The Control (Ctrl) is c-PARP.
Figure 1G:
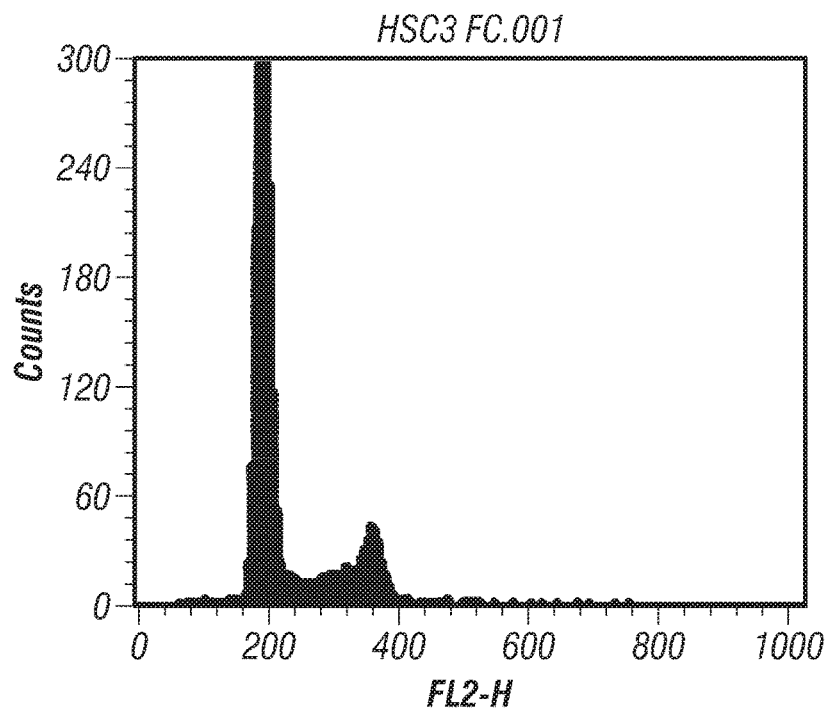
Figure 1:
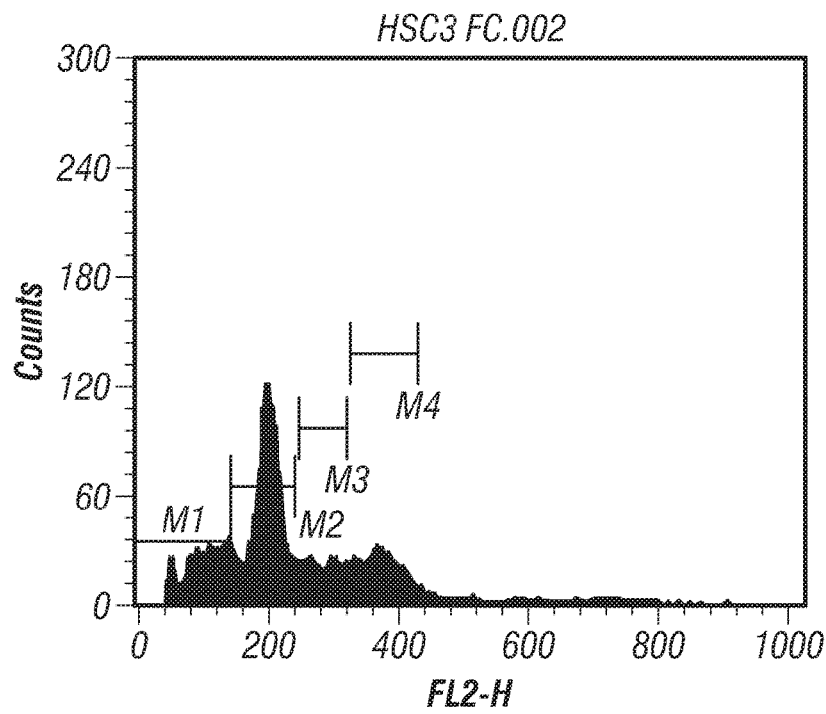
Figure 1G:
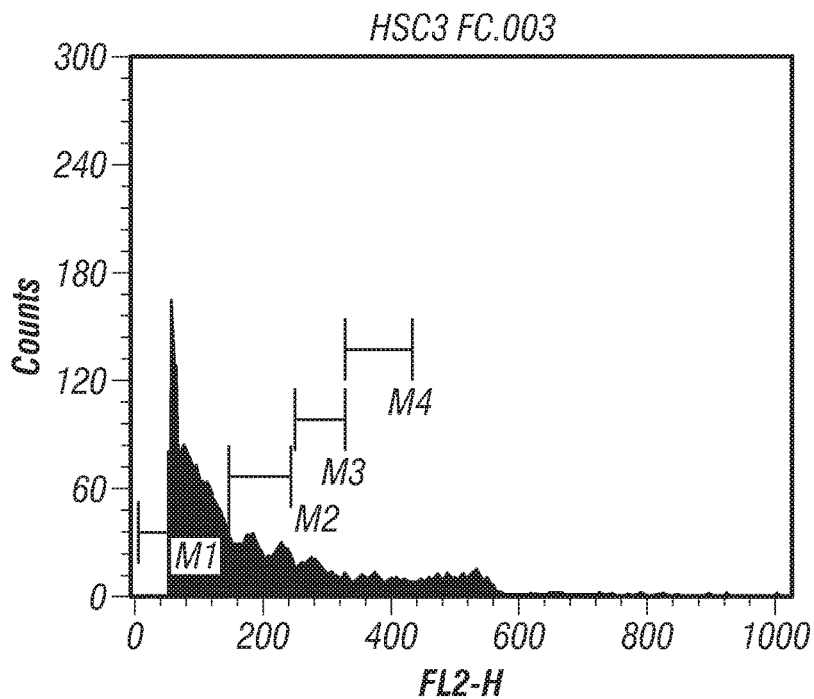
Figure 1:
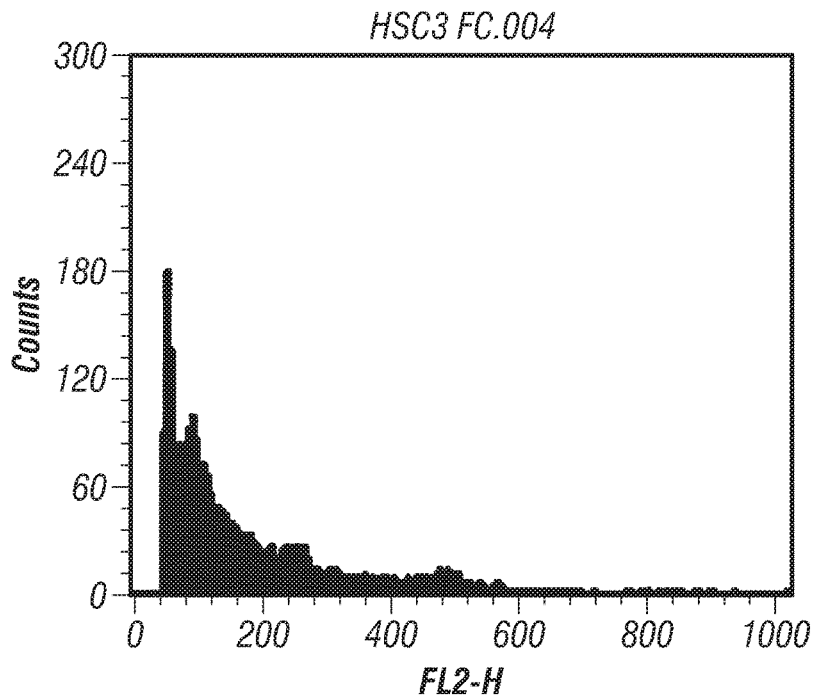
Figures 1, 1H:
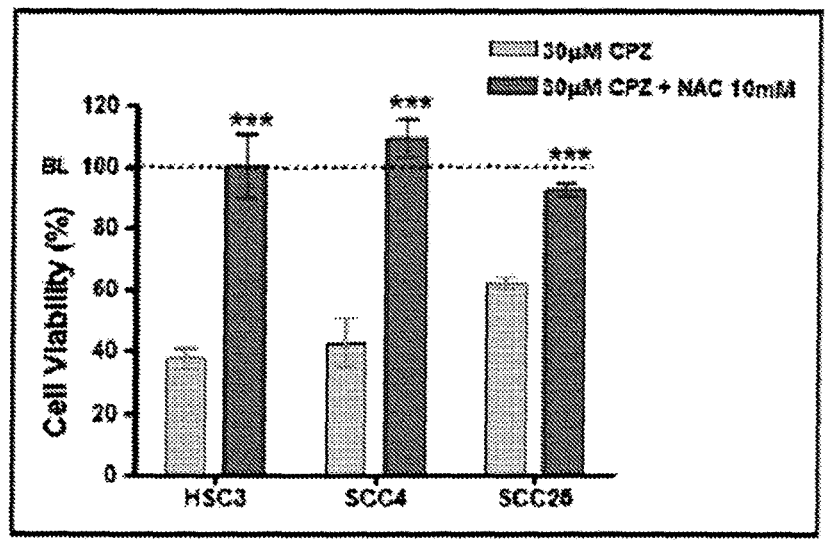
Figures 1, 1H, 2:
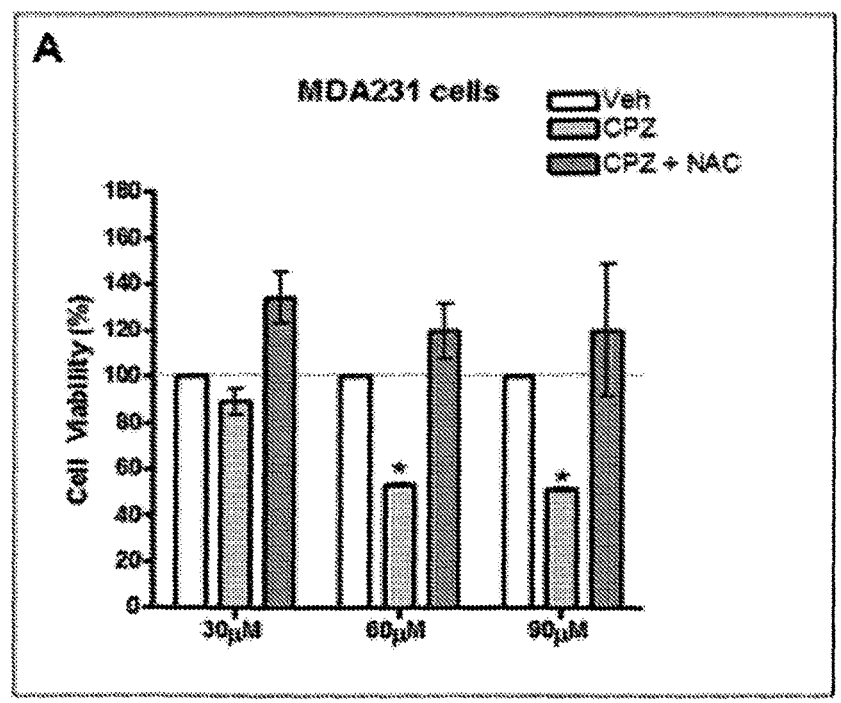
Figures 1, 1H, 2, 3:
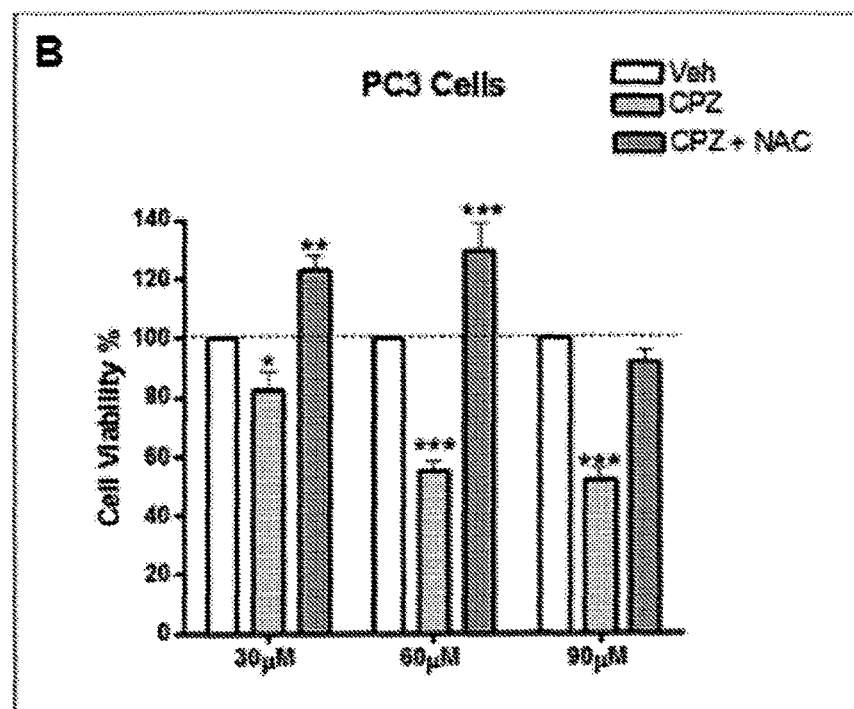
Figures 1, 1I:
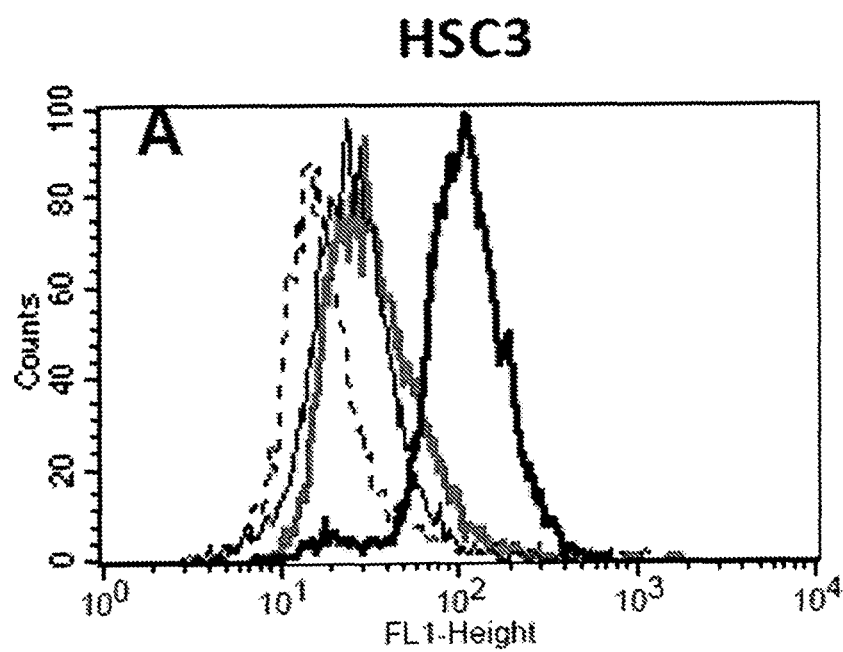
Figures 1, 1I, 2:
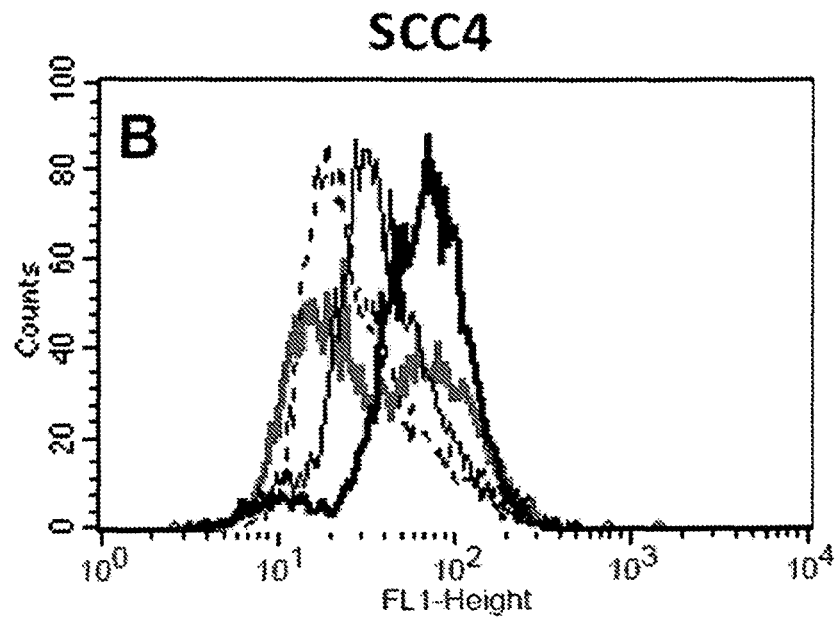
Figures 1, 1I, 2, 3:
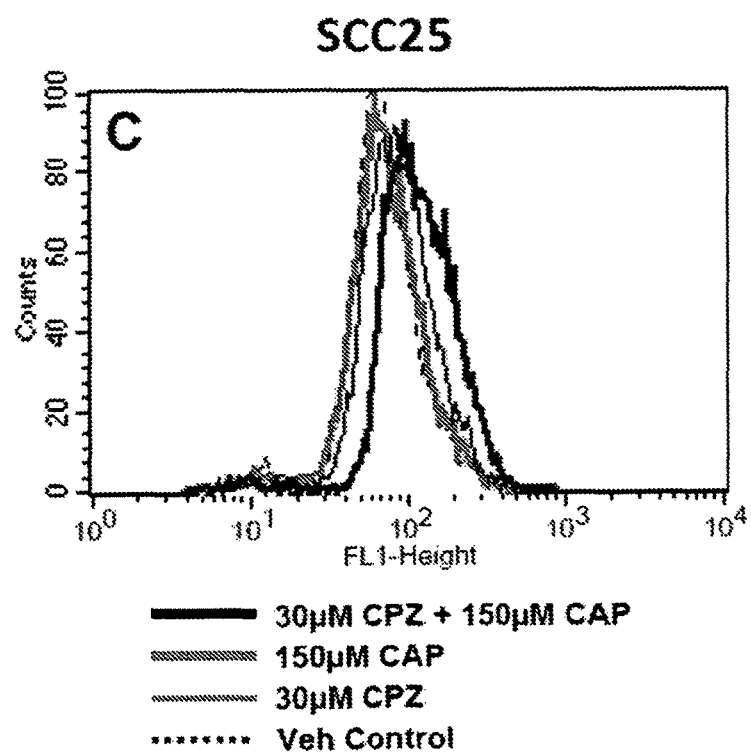
Figures 1A, 1J:
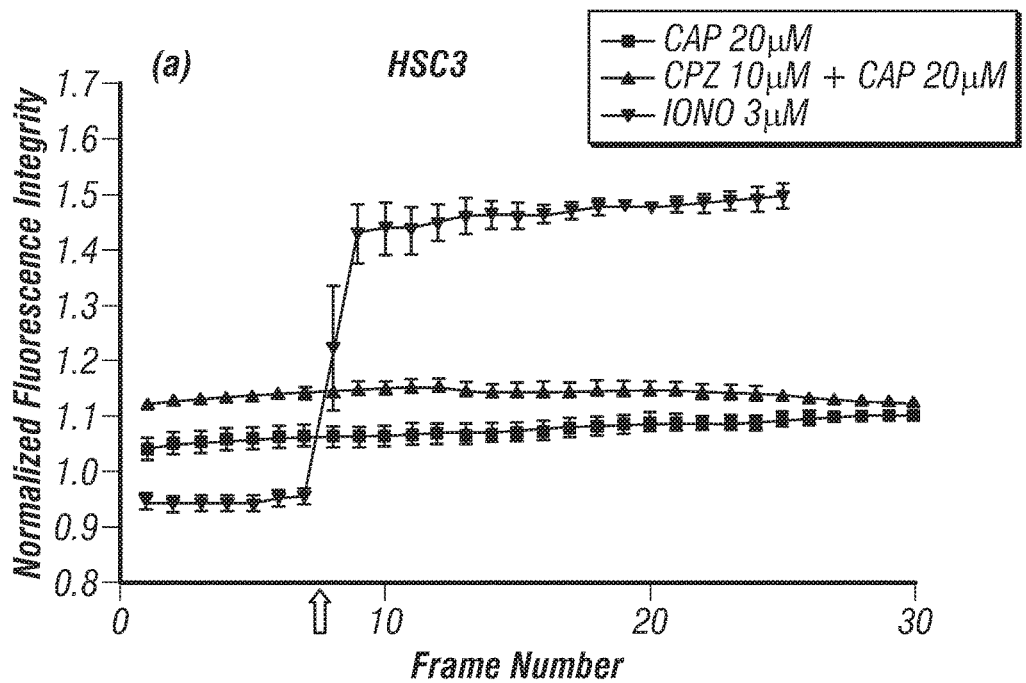
Figures 1B, 1J:
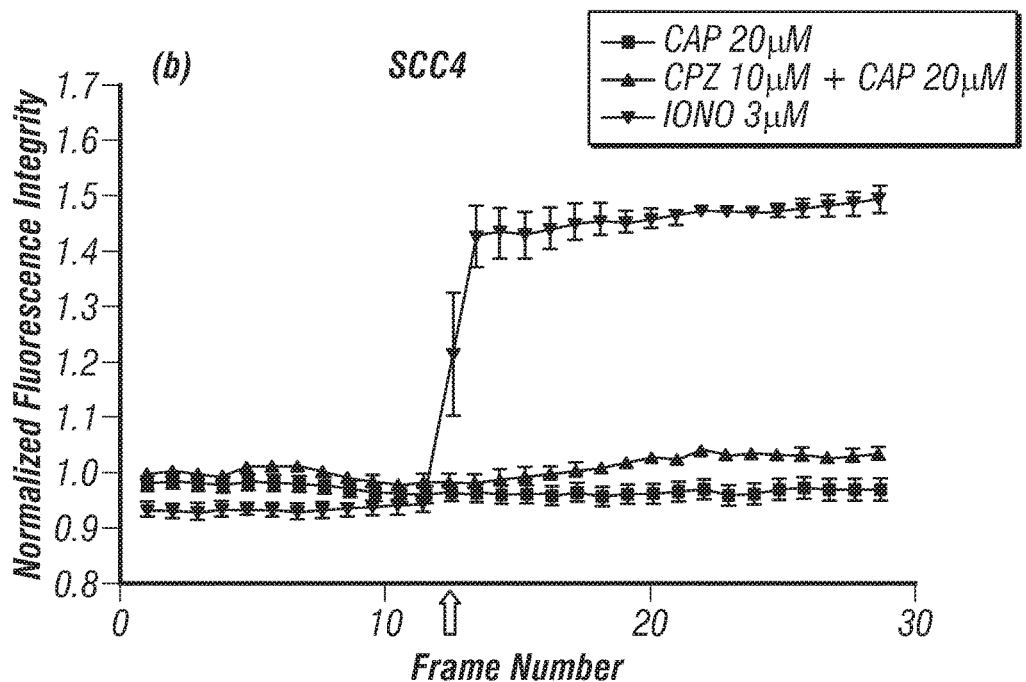
Figures 1C, 1J:
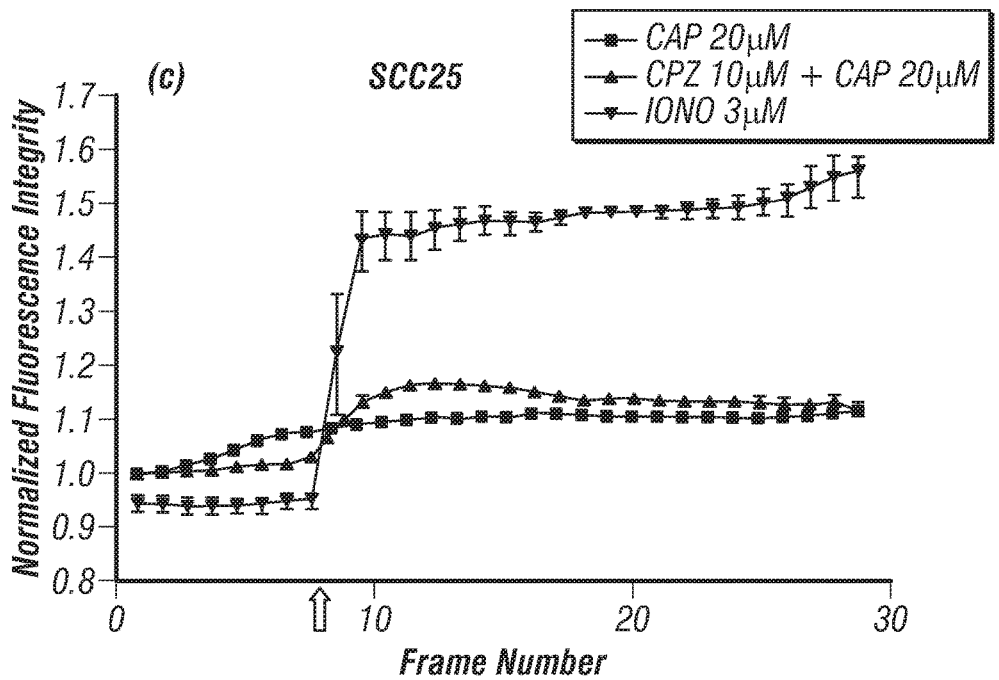
Figures 1, 1J, 2, 2A:
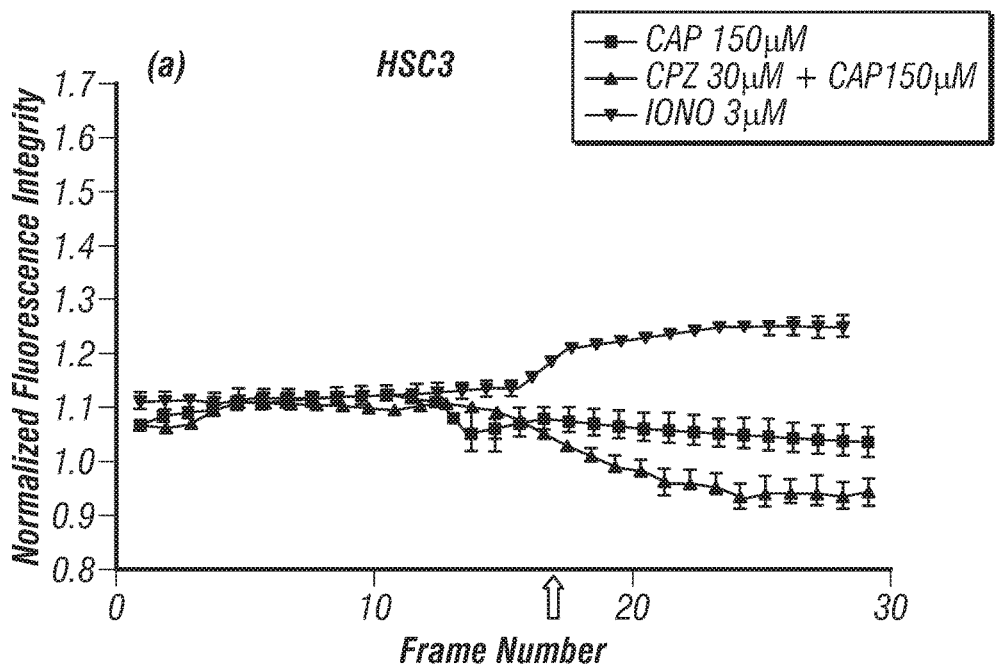
Figures 1, 1J, 2, 2B:
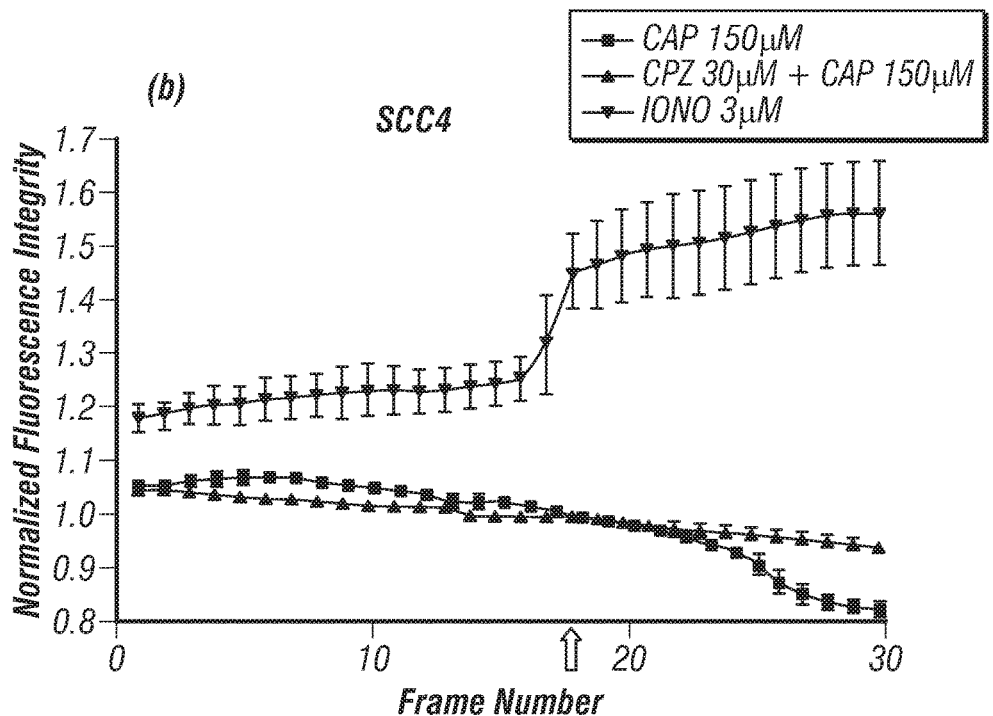

These apoptosis studies also revealed cell cycle arrest in the M1 (subG1) phase of mitosis—with apoptotic figures evident microscopically. In particular, OSCC cells treated with CPZ at 30 µM, 60 µM, or 90 µM for 24 hours undergo apoptosis as shown by the general increase in the percent of cells in SubG1 phase (M1 phase) when flow sorted (cells were harvested and fixed in 70% ethanol, after which the cells were treated with RNase A, stained with propidium iodide, and subjected to cell cycle analysis using DNA profile FACS for SubG1, G1, and S+G2/M phase determinations—results for HSC3, SCC4, and SCC25 cells are shown in Table 1; western blot analysis (FIG. 1F) revealed increasing levels of cleaved PARP [poly (ADP-ribose) polymerase] in treated cells—consistent with apoptosis. In particular, Table 1 provides additional cell cycle distribution data of OSCC cells (%) treated with 0 µM, 30 µM, 60 µM, or 90 µM CPZ for 24 hours. Data for OSCC cell lines HSC3, SCC4, and SCC25 are also provided in diagrams of FIGS. 1G-1, 1G-2, and 1G-3, respectively.

TABLE 1

Additional Cell Cycle Distribution Data

| CPZ µM | SubG1 | G0/G1 | S | G2/M |
| --- | --- | --- | --- | --- |
| HSC3 | | | | |
| 0 | 0.61 | 78.21 | 9.14 | 12.04 |
| 30 | 18.47 | 47.76 | 13.47 | 20.3 |
| 60 | 57.31 | 24.09 | 11.23 | 7.37 |
| 90 | 61.12 | 23.53 | 10.27 | 5.08 |
| SCC4 | | | | |
| 0 | 0.89 | 67.54 | 14.54 | 17.03 |
| 30 | 2.01 | 70.77 | 15.08 | 12.14 |
| 60 | 33.72 | 21.03 | 21.04 | 24.21 |
| 90 | 27.99 | 15.61 | 24.83 | 31.57 |//
| SCC25 | | | | |
| 0 | 32.60 | 58.06 | 5.17 | 4.17 |
| 30 | 44.77 | 42.92 | 9.01 | 3.3 |
| 60 | 50.48 | 28.63 | 14.78 | 6.11 |
| 90 | 69.91 | 17.23 | 10.36 | 2.5 |

B. Knock-Down Studies

Figures 1, 1J, 2, 2C:
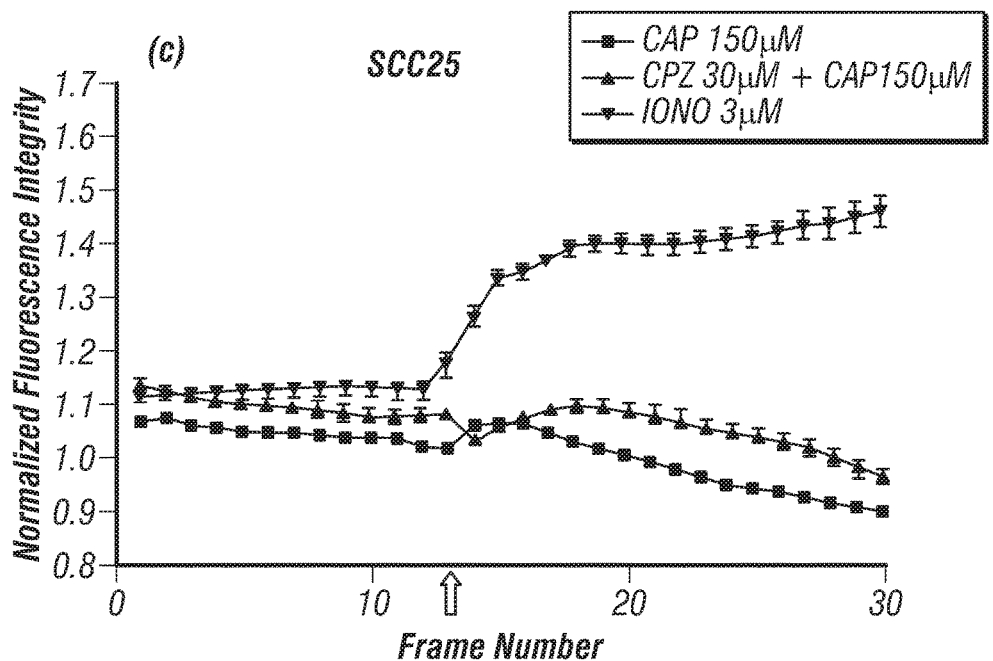
Figure 3A:
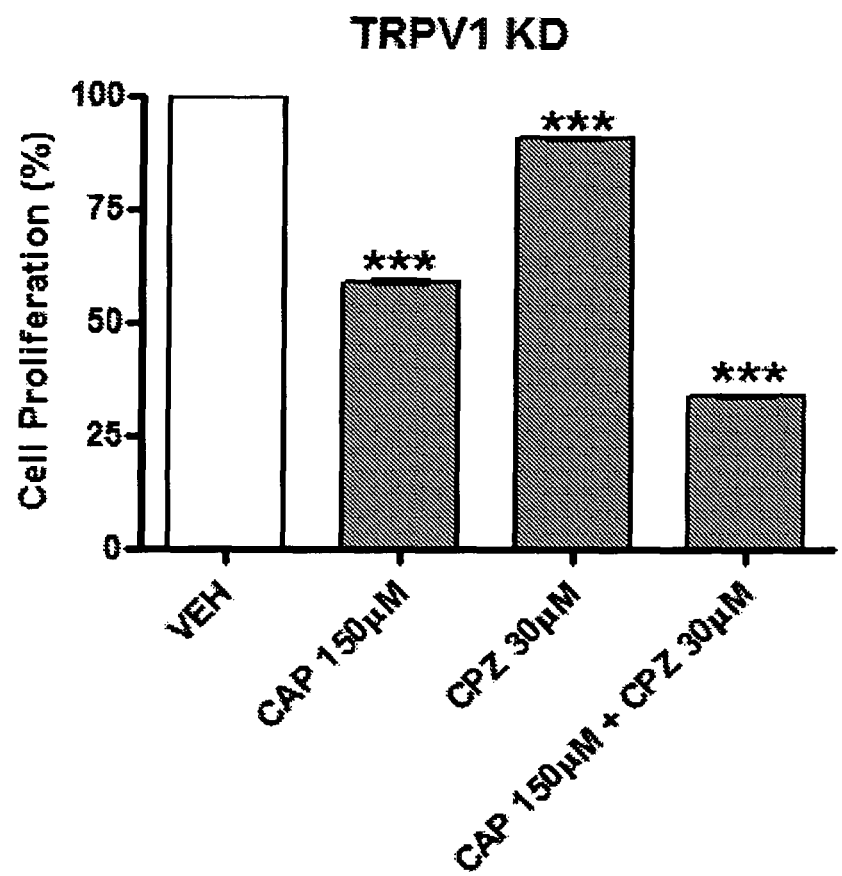
FIG. 3A. TRPV1 Knock-down in SCC25 cells. Cell proliferation assays of SCC25 cells transfected with TRPV1 siRNA and treated with: 150 μM CAP [CAP 150 μM]; 30 μM CPZ [CPZ 30 μM]; or 150 μM CAP plus 30 μM CPZ [CAP 150 μM+CPZ 30 μM]. VEH=delivery vehicle control without CAP or CPZ. ***p<0.001.
Figure 3B:
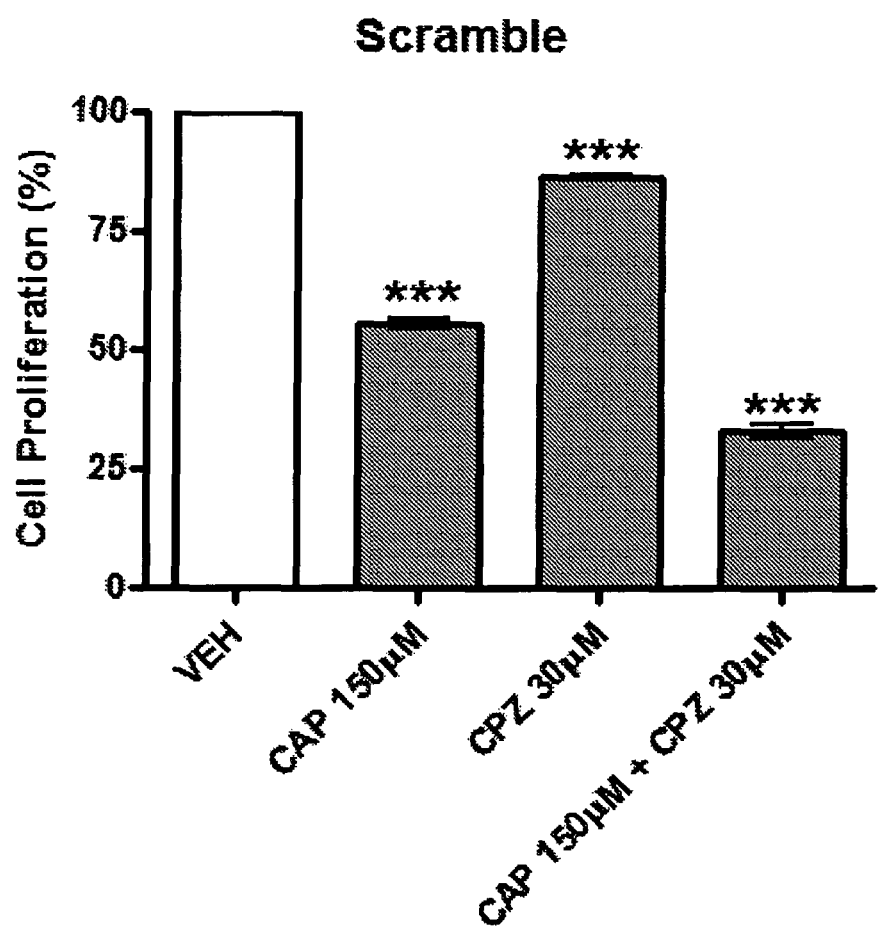
FIG. 3B. Cell proliferation assays of SCC25 cells transfected with scramble siRNA (control) and treated with: 150 μM CAP [CAP 150 μM]; 30 μM CPZ [CPZ 30 μM]; or 150 μM CAP plus 30 μM CPZ [CAP 150 μM+CPZ 30 μM]. VEH=delivery vehicle control without CAP or CPZ. ***p<0.001. Control assays for SCC25 cells transfected with TRPV1 siRNA of FIG. 3A.
Figure 3C:
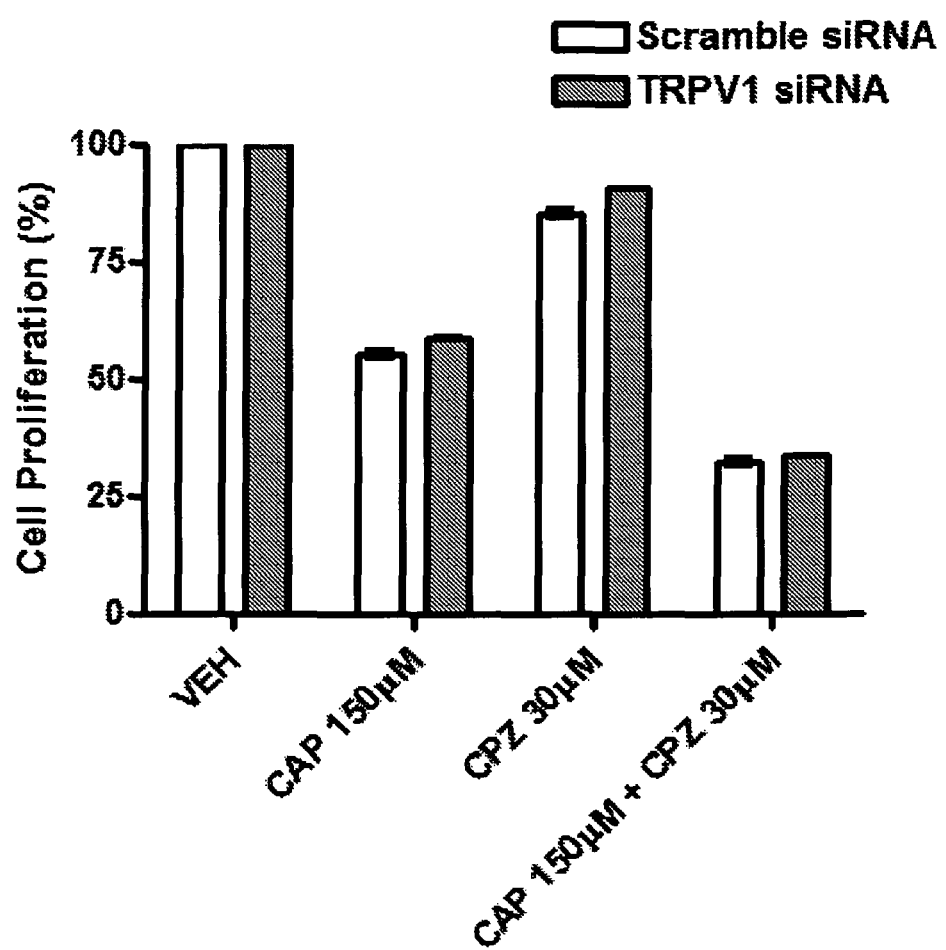
FIG. 3C. Comparison of cell proliferation assays of SCC25 cells transfected with scramble siRNA (control) or TRPV1 siRNA and treated with: 150 μM CAP [CAP 150 μM]; 30 μM CPZ [CPZ 30 μM]; or 150 μM CAP plus 30 μM CPZ [CAP 150 μM+CPZ 30 μM]. Reduced TRPV1 expression in SCC25 cells generally does not alter the viability of SCC25 cells treated with CAP and/or CPZ compared to control. VEH=delivery vehicle control without CAP or CPZ.

To better understand the mechanism of action of CAP and CPZ, knock-down studies were performed using siRNA against TRPV1 followed by treatment with CAP and/or CPZ. These studies confirmed that TRPV1 agonists/antagonists reduce OSCC cell viability in a manner independent of TRPV1 interactions. In addition, CPZ was found to be more effective than CAP in reducing cell proliferation (see FIGS. 2A, 2B, and 2C for data on knock-down studies using HSC3 cells; and see FIGS. 3A, 3B, and 3C for data on knock-down studies using SCC25 cells).

It is hypothesized that CPZ and CAP are inhibitory analogs of coenzyme Q, and that these molecules effectively block the electron transport chain—thereby generating reactive oxygen species (ROS) and subsequently inducing apoptosis (Ziglioli, et al., 2009). To test this hypothesis, the effects of CPZ on OSCC cell lines treated with the antioxidant N-Acetyl-Cysteine (NAC) (10 mM) were evaluated. NAC was found to reverse significantly the effects of CPZ on all OSCC cell lines tested as well as MDA231 breast cancer cells and P3 prostate cancer cells—indicating that ROS most likely are causing apoptosis in treated cells. (See FIGS. 1H-1 to 1H-3). Relatedly, ROS assays were performed for OSCC lines by flow cytometry and an increase was measured in cells treated with CPZ and CAP. (See FIGS. 1I-1 to 1I-3). Moreover, a reversal was indicated upon treatment with NAC. (See FIGS. 1I-4 to 1I-6, comparing (a) to (b)). Lastly, calcium imaging data of OSCC cell lines indicate that TPRV-1 channels are not functional in the tested cell lines. (See FIGS. 1J-1(a) to (c) and FIG. 1J-2(a) to (c). Taken together, this data revealed that both CAP and CPZ induce apoptosis in OSCC cells through the generation of ROS, i.e., in a manner that is independent of TRPV1 interactions.

Figure 1K:
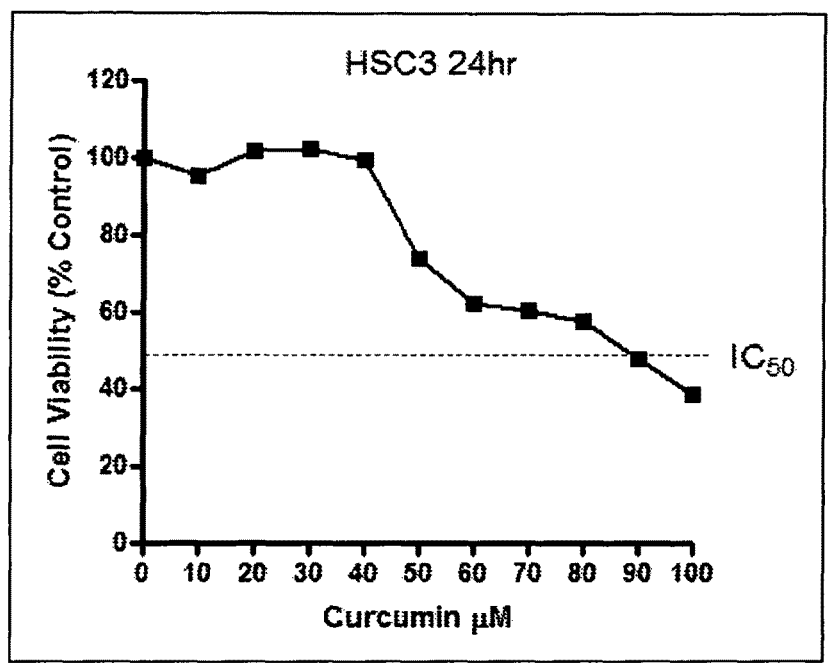
FIG. 1K. Cell viability assay of HSC3 cells treated with increasing concentrations of curcumin; $IC_{50}=90$ μM. The dose response curve demonstrates that curcumin reduces cell viability in HSC3 OSCC cells at lower concentrations than CAP but not as effectively as CPZ. By comparison, CAP $IC_{50}$ is about 150 μM and CPZ $IC_{50}$ is 30 μM.
Figure 2A:
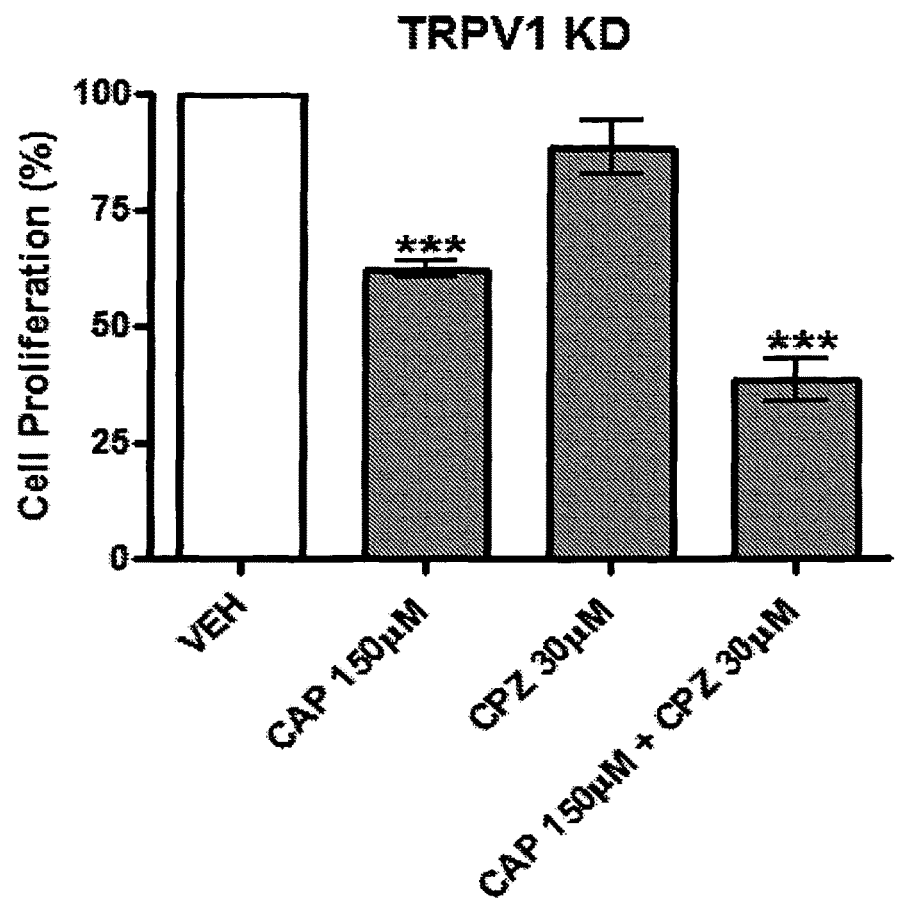
Figure 2B:
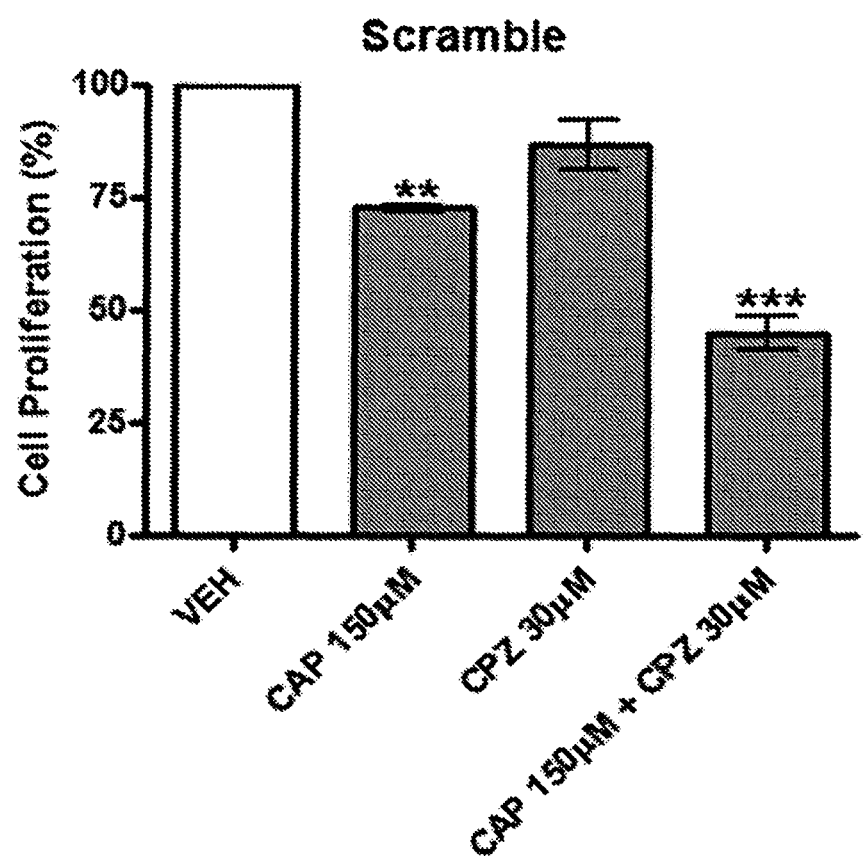
FIG. 2B. Cell proliferation assays of HSC3 cells transfected with scramble siRNA (control) and treated with: 150 μM CAP [CAP 150 μM]; 30 μM CPZ [CPZ 30 μM]; or 150 μM CAP plus 30 μM CPZ [CAP 150 μM+CPZ 30 μM]. VEH=delivery vehicle control without CAP or CPZ. p<0.01, *p<0.001. Control assays for HSC3 cells transfected with TRPV1 siRNA of FIG. 2A.
Figure 2C:
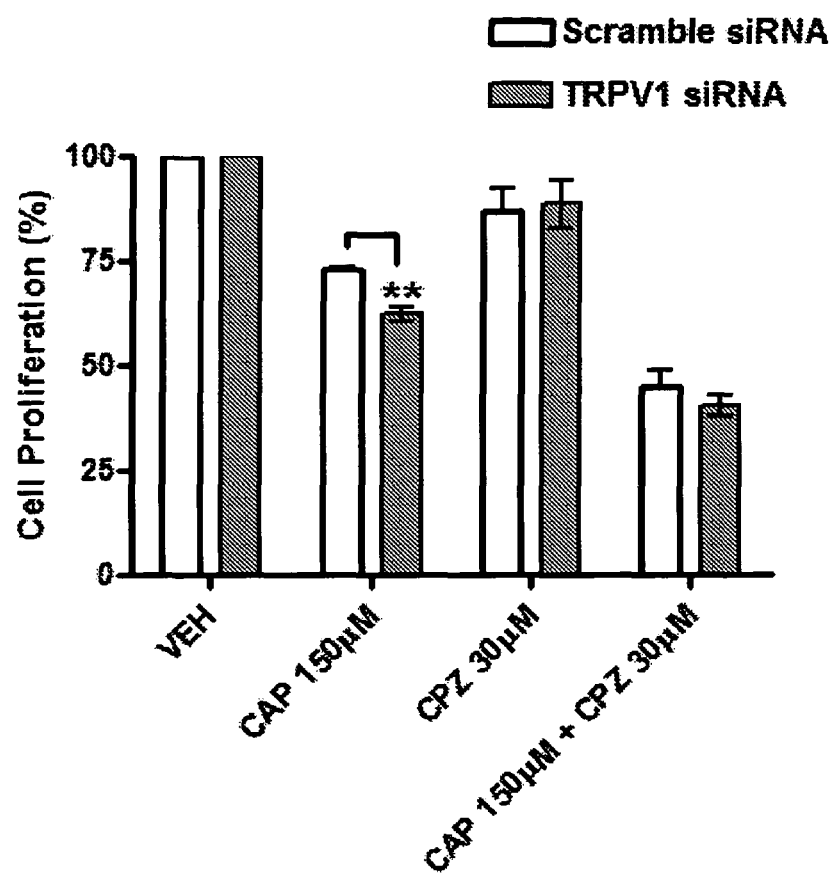
FIG. 2C. Comparison of cell proliferation assays of HSC3 cells transfected with scramble siRNA (control) or TRPV1 siRNA and treated with: 150 μM CAP [CAP 150 μM]; 30 μM CPZ [CPZ 30 μM]; or 150 μM CAP plus 30 μM CPZ [CAP 150 μM+CPZ 30 μM]. Reduced TRPV1 expression in HSC3 cells generally does not alter the viability of HSC3 cells treated with CAP and/or CPZ compared to control. VEH=delivery vehicle control without CAP or CPZ. **p<0.01.

CPZ, however, is indicated as being more effective than CAP. $IC_{50}$ is 30 µM for CPZ and 150 µM for CAP. In addition, $IC_{50}$ is 90 µM for curcumin. (See FIG. 1K.)

Additional exemplary materials and methods for reducing cancerous tumor cell growth, wherein method includes administering an effective amount of a composition comprising CPZ or an analog of CPZ to a subject having or suspected of having cancerous tumor cell growth, are disclosed in the Examples herein.

C. Methods of Using Compositions Comprising CPZ or an Analog of CPZ

"Treatment" and "treating" refer to administration or application of a therapeutic agent to a subject or performance of a procedure or modality on a subject for the purpose of obtaining a therapeutic benefit for a disease or health-related condition. For example, the compositions comprising CPZ or an analog of CPZ of the present invention may be administered to a subject for the purpose of reducing cancerous tumor cell growth in a subject.

The terms "therapeutic benefit," "therapeutically effective" or "effective amount" refer to the promotion or enhancement of the well-being of a subject. This includes, but is not limited to, a reduction in the frequency or severity of the signs or symptoms of a disease, such as one having a relationship with cancerous tumor cell growth. For example, administering compositions comprising CPZ or an analog of CPZ of the present invention may reduce the signs and symptoms of a condition associated with cancerous tumor cell growth.

"Prevention" and "preventing" are used according to their ordinary and plain meaning. In the context of a particular disease or health-related condition, those terms refer to administration or application of an agent, drug, or remedy to a subject or performance of a procedure or modality on a subject for the purpose of preventing or delaying the onset of a disease or health-related condition. For example, one embodiment includes administering compositions comprising CPZ or an analog of CPZ of the present invention to a subject having or suspected of having cancerous tumor cell growth.

Compositions comprising CPZ or an analog of CPZ, as disclosed herein, may be used to treat any disease or condition for which a composition comprising CPZ or an analog of CPZ is contemplated as being effective for treating or preventing the disease or condition. Such a disease or condition may include a cell hyperproliferative disease or condition.

D. Pharmaceutical Preparations

Certain methods and compositions set forth herein are directed to administration of an effective amount of a composition comprising CPZ or an analog of CPZ.

1. Compositions

A "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it needs to be sterile for such routes of administration as injection.

The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations should meet sterility, pyrogenicity, general safety and purity standards as required by FDA Office of Biologics standards.

The formulation of the composition may vary depending upon the route of administration. For parenteral administration in an aqueous solution, for example, the solution should be suitably buffered if necessary and the liquid diluent first rendered isotonic with sufficient saline or glucose. In this connection, sterile aqueous media that can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal, biodegradable polymer, and nanoparticle formulations; enteric coating formulations; time release capsules; formulations for administration via an implantable drug delivery device, topical creams, and any other form. One may also use nasal solutions or sprays, aerosols or inhalants in the present invention.

The capsules may be, for example, hard shell capsules or soft-shell capsules. The capsules may optionally include one or more additional components that provide for sustained release. In some of these aspects, compositions comprising CPZ or an analog of CPZ may further include a hydrophilic, swellable, hydrogel forming material. Such compositions may be encased in a coating that includes a water insoluble polymer and a hydrophilic water permeable agent. In some embodiments, the water insoluble polymer is a methyl methacrylate-methacrylic acid copolymer.

In certain embodiments, pharmaceutical composition includes at least about 0.1% by weight of the active compound. In other embodiments, the pharmaceutical composition includes about 2% to about 75% of the weight of the composition, or between about 25% to about 60% by weight of the composition, for example, and any range derivable therein.

The compositions may comprise various antioxidants to retard oxidation of one or more components. Additionally, the prevention of the action of microorganisms can be accomplished by preservatives such as various antibacterial and antifungal agents, including but not limited to parabens (e.g., methylparabens, propylparabens), chlorobutanol, phenol, sorbic acid, thimerosal or combinations thereof. The composition should be stable under the conditions of manufacture and storage, and preserved against the contaminating action of microorganisms, such as bacteria and fungi.

In certain preferred embodiments, an oral composition may comprise one or more binders, excipients, disintegration agents, lubricants, flavoring agents, and combinations thereof. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

In particular embodiments, prolonged absorption can be brought about by the use in the compositions of agents delaying absorption, such as, for example, aluminum monostearate, gelatin, or combinations thereof.

2. Routes of Administration

Upon formulation, solutions will be administered in a manner compatible with the dosage formulation and in such amount as is therapeutically effective.

The composition can be administered to the subject using any method known to those of ordinary skill in the art. For example, a pharmaceutically effective amount of the composition may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (Remington's, 1990).

In particular embodiments, the composition is administered to a subject using a drug delivery device. Any drug delivery device is contemplated for use in delivering an effective amount of a composition comprising CPZ or an analog of CPZ to a subject having or suspected of having cancerous tumor cell growth for reducing cancerous tumor cell growth in the subject.

3. Dosage

A pharmaceutically effective amount of a composition comprising CPZ or an analog of CPZ is determined based on the intended goal. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

The amount of a composition comprising CPZ or an analog of CPZ (or a derivative) to be administered will depend upon the cancerous tumor cell growth or other disease to be treated, the length of duration desired and the bioavailability profile of the implant, and the site of administration. Generally, the effective amount will be within the discretion and wisdom of the patient's physician. Guidelines for administration include dose ranges of from about 0.01 mg to about 500 mg of CPZ or an analog of CPZ.

For example, a dose of CPZ or an analog of CPZ may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be pre-operative, intra-operative, or post-operative.

4. Secondary and Combination Treatments

Certain embodiments provide for the administration or application of one or more secondary or additional forms of therapies. The type of therapy is dependent upon the specific type of cancerous tumor cell growth or other disease that is being treated or prevented. The secondary form of therapy may be administration of one or more secondary pharmacological agents that can be applied in the treatment or prevention of cancerous tumor cell growth or a disease, disorder, or condition associated with cancerous tumor cell growth. For example, the secondary or additional form of therapy may be directed to treating pain, inflammation, or even high blood pressure, high cholesterol, high blood sugar (or diabetes), an autoimmune disease, an inflammatory disease, a cardiovascular condition, or a peripheral vascular condition. In certain embodiments, the secondary or additional form of therapy may be directed to inhibition of coenzyme Q. Coenzyme Q inhibitors include lipid-lowering drugs such as the statins (lovastatin, pravastatin, and simvastatin) and gemfibrozil, as well as agents that lower blood sugar, such as glyburide and tolazamide. Additionally drugs such as beta-blockers, that can inhibit coenzyme Q-dependent enzyme reactions, may offer synergistic effects in combination with CPZ or CPZ analog therapy for cancerous tumor cell growth.

If the secondary or additional therapy is a pharmacological agent, it may be administered prior to, concurrently with, or following administration of the composition comprising CPZ or an analog of CPZ.

The interval between administration of the composition comprising CPZ or an analog of CPZ and the secondary or additional therapy may be any interval as determined by those of ordinary skill in the art. For example, the composition comprising CPZ or an analog of CPZ and the secondary or additional therapy may be administered simultaneously, or the interval between treatments may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the timing of administration of a secondary therapeutic agent is determined based on the response of the subject to the composition comprising CPZ or an analog of CPZ.

E. Kits

Kits are also contemplated as being used in certain aspects of the present invention. For instance, a composition comprising CPZ or an analog of CPZ of the present invention can be included in a kit. A kit can include a container.

Containers can include a bottle, a metal tube, a laminate tube, a plastic tube, a dispenser, a pressurized container, a barrier container, a package, a compartment, or other types of containers such as injection or blow-molded plastic containers into which hydrogels are retained. The kit can include indicia on its surface. The indicia, for example, can be a word, a phrase, an abbreviation, a picture, or a symbol.

Further, the compositions comprising CPZ or an analog of CPZ of the present invention may also be sterile, and the kits containing such compositions can be used to preserve the sterility. The compositions may be sterilized via an aseptic manufacturing process or sterilized after packaging by methods known in the art.

F. Capsazepine

CPZ, a competitive antagonist of CAP, competes for the CAP-binding site on TRPV1. Structure-activity relationship for CAP-related compounds have been rationalized by dividing the CAP molecule into three regions—the A (aromatic ring)-, B (amide bond)-, and C (hydrophobic side chain)-regions (e.g., see Walpole, et al., 1994). CAP may be diagrammed structurally as follows:

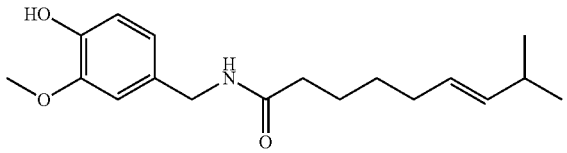 [SMILES: COc1cc(CNC(=O)CCCC/C=C/C(C)C)ccc1O]

CPZ may be viewed as a derivative of CAP in which the amide bond of CAP is replaced by a thiourea moiety and a propylidene linker between the aromatic vanillyl 2-carbon A-ring and the B-linker amide nitrogen forces the aromatic ring in an orthogonal orientation with respect to the thiourea bond (Szallasi & Appendino, 2004). This constraint has long been considered as the distinctive characteristic of vanilloid antagonism (Tominaga & Malmberg, 1998).

An analog of CPZ that is useful in a composition for reducing cancerous tumor cell growth through administration of an effective amount to a subject having or suspected of having cancerous tumor cell growth, may also share this constraint that is distinctive of vanilloid antagonism. However, an effective analog of CPZ may lack this constraint in that both CAP and CPZ induce apoptosis in OSCC cells (and apparently other cancer cells) in a manner that is independent of TRPV1 interactions and indicated to be through the generation of ROS. In this light, a CPZ analog comprises a compound structurally similar to CPZ and, like CPZ, induces apoptosis in OSCC cells (or other cancerous cells). In other embodiments, a CPZ analog can also be a CAP derivative that induces apoptosis in OSCC cells (or other cancerous cells). In various embodiments, a CPZ analog can comprise, e.g., SB-366791 (cinnamide analog), AMG-9810 (cinnamide analog), A-425619 (urea analog), BCTC (urea analog), or JNJ-17203212 (urea analog), (see Table 2). In various embodiments, a CPZ analog can comprise analogs that function like CPZ in inducing apoptosis in OSCC cells (or other cancer cells) through the generation of ROS even though it is potentially less structurally similar to CPZ. In various embodiments, a CPZ analog can comprise, e.g., SB-705498 (urea analog), quinazoline analog, Compound 46ad (benzimidazol analog), Compound 26 (quinazolinon analog), AMG 517, or NGD 8243. (see Table 3; see generally Tables 3a and 3b of Szallasi, et al., 2007). In various embodiments, TRPV1 antagonist would also be an analog of CPZ.

Data from Tables 3a and 3b of Szallasi A et al., 2007 are included herein as follows in Tables 2 and 3, respectively:

TABLE 2

| Name | Structure | Comments | References |
|---|---|---|---|
| Capsazepine (thiourea) | 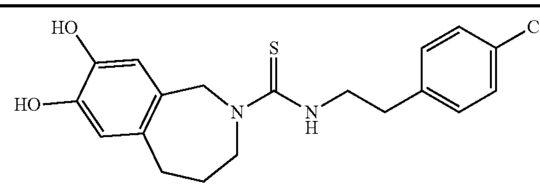 | rIC$_{50}$ = 420 nM ($^{45}$Ca$^{2+}$ uptake) | 32 |
| | | Inhibitis voltage-activated calcium channels and nicotinic acetylcholine receptors | 30, 31 |
| | | Significantly reversed CFA-induced mechanical hyperalgesia in guinea pigs | 29 |
| SB-366791 (cinnamide analog) | 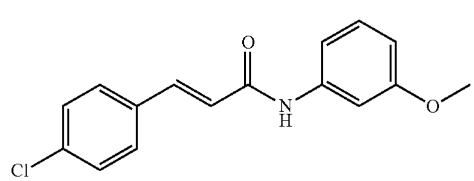 [SMILES: COc1cccc(NC(=O)/C=C/c2ccc(Cl)cc2)c1] | hK$_i$ = 18 nM (FLIPR) Selective versus TRPV4 and other TRP channels Inhibits capsaicin and heat-mediated activation of TRPV1 | 33 |
| AMG-9810 (cinnamide analog) | 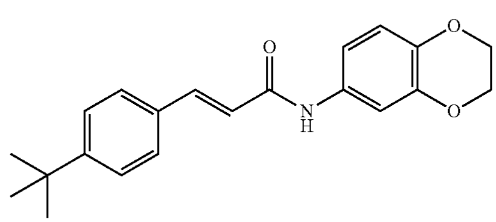 [SMILES: CC(C)(C)c1ccc(/C=C/C(=O)Nc2ccc3c(c2)OCCO3)cc1] | hIC$_{50}$ = 25 nM ($^{45}$Ca$^{2+}$ uptake) hIC$_{50}$ of > 4 μM at TRPV3, TRPV4, TRPA1 and TRPM8 Inhibits CFA-induced thermal (30 mg per kg) and mechanical hyperalgesia (100 mg per kg) | 34 |

TABLE 2-continued

TRPV1 Antagonists

| Name | Structure | Comments | References |
|---|---|---|---|
| A-425619 (urea analog) | 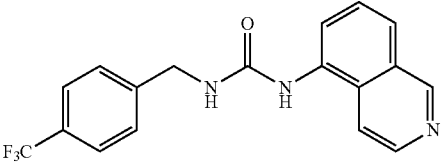 [SMILES: O=C(NCc1ccc(C(F)(F)F)cc1)Nc1cccc2cnccc12] | $hIC_{50}$ = 5 nM (FLIPR) TRPM8 $IC_{50}$ = 8 μM; TRPA1 $IC_{50}$ > 10 μM Inhibits CFA-induced thermal hyperalgesia ($ED_{50}$ = 10 mg per kg) | 34 27 |
| BCTC (urea analog) | 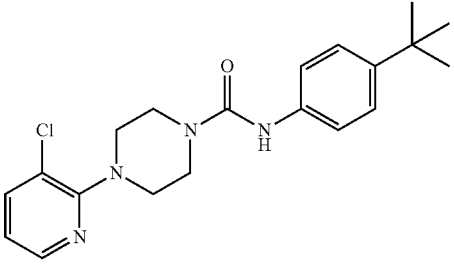 [SMILES: CC(C)(C)c1ccc(NC(=O)N2CCN(c3ncccc3Cl)CC2)cc1] | $hIC_{50}$ = 35 nM (FLIPR) TRPM8 $IC_{50}$ = 143 nM; Inhibits CFA-induced thermal & mechanical hyperalgesia (3-30 mg per kg, orally) Reduces tactile allodynia & thermal hyperalgesia in a partial nerve-ligation model | 35 22 28 |
| JNJ-17203212 (urea analog) | 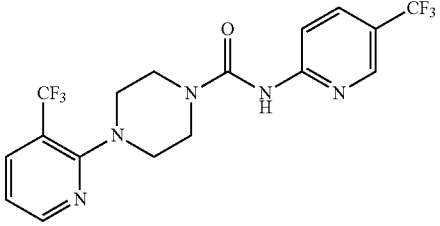 [SMILES: O=C(Nc1ccc(C(F)(F)F)cn1)N1CCN(c2ncccc2C(F)(F)F)CC1] | $hIC_{50}$ = 65 nM (FLIPR) Elicits ~1° C. increase in core body temperature in rats (30 mg per kg, orally) Attenuates nocifensive behaviors in an in vivo model of bone-cancer pain | 24 25 |

TABLE 3

Additional TRPV1 Antagonists

| Name | Structure | Comments | References |
|---|---|---|---|
| SB-705498 (urea analog) | 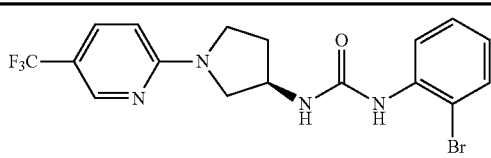 | $rIC_{50}$ = 32 nM (FLIPR) Phase I: reduced capsaicin-evoked flare and acute heat-evoked pain on non-sensitized skin | 36 23 |
| Quinazoline analog | 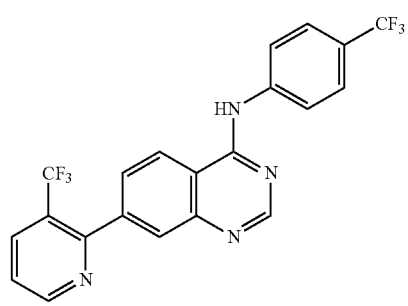 [SMILES: FC(F)(F)c1ccc(Nc2ncnc3cc(-c4ncccc4C(F)(F)F)ccc23)cc1] | $hIC_{50}$ = 1 nM (FLIPR) Achieved 80% block of carrageenan-induced thermal hyperalgesia at 3 mg per kg (MED 0.1 mg per kg) | 37 |

TABLE 3-continued

Additional TRPV1 Antagonists

| Name | Structure | Comments | References |
|---|---|---|---|
| Compound 46ad (benzimidazol analog) | 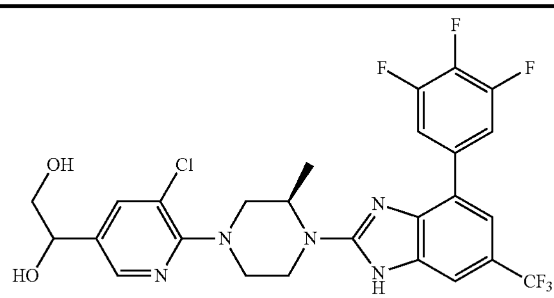 | $hIC_{50}$ = 1 nM ($^{45}Ca^{2+}$ uptake) Achieved significant reversal of CFA-induced thermal hyperalgesia (30 mg per kg, orally) | 38 |
| Compound 26 (quinazolinon analog) | 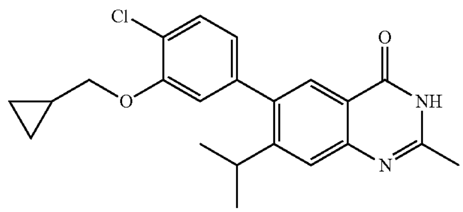 [SMILES: Cc1nc2cc(C(C)C)c(-c3ccc(Cl)c(OCC4CC4)c3)cc2c(=O)[nH]1] | $hIC_{50}$ = 50 nM (low pH activation) Achieved 60% reversal of CFA-induced mechanical hyperalgesia (30 mg per kg, orally) Achieved 57% reversal of mechanical hyperalgesia in a partial nerve-ligation model | 26 |
| AMG 517 | 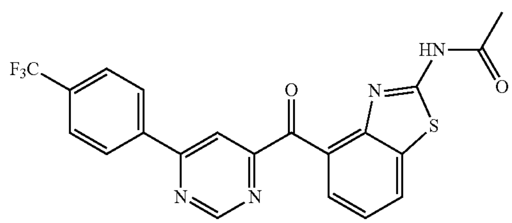 [SMILES: CC(=O)Nc1nc2c(C(=O)c3cc(-c4ccc(C(F)(F)F)cc4)ncn3)cccc2s1] | Initiation of Phase I clinical trials reported in September 2004 $hIC_{50}$ = 0.9 nM ($^{45}Ca^{2+}$ uptake) Achieved ~40% block of CFA-induced thermal hyperalgesia at 10 mg per kg (MED 1 mg per kg) | M. Norman |
| NGD 8243 | 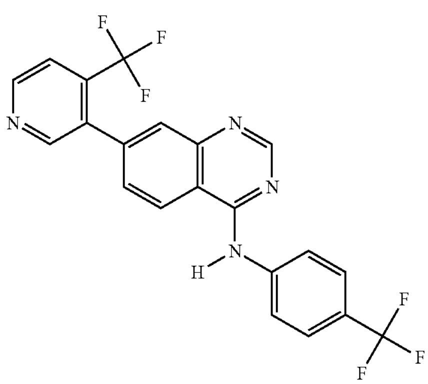 [SMILES: FC(F)(F)c1ccc(Nc2ncnc3cc(-c4cnccc4C(F)(F)F)ccc23)cc1] | Initiation of Phase II trials announced in November 2006 | Neutrogen, press release |

(NGD 8243 structure from NCBI PubChem database-2D Structure)

For Tables 2 and 3, the following abbreviations are provided: BCTC, N-(4-tertiarybutylphenyl)-4-(3-chloropyridin-2-yl)tetrahydropyrazine-1(2H)-carboxamide; CFA, complete Freund's adjuvant; $ED_{50}$, half-maximal effective dose; FLIPR, fluorescence imaging plate reader; $hIC_{50}$, half maximal inhibitory concentration in humans; $hK_i$, inhibition constant in humans; MED, minimum effective dose; $rIC_{50}$, half maximal inhibitory concentration in rats; TRP, transient receptor potential receptor; TRPA1, TRP subfamily ankyrin, member 1; TRPM8, TRP receptor subfamily melastatin, member 8; TRPV1,3,4, TRP receptor subfamily vanilloid, member 1,3, or 4.

EXAMPLES

The following examples are included to demonstrate certain non-limiting aspects of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

OSCC Mouse Xenograft Models

In order to evaluate the effects of CPZ on OSCC in vivo, mouse xenograft models were generated using multiple OSCC cell lines. These mouse xenograft models were treated with CPZ for two weeks. Dramatic reduction in tumor growth was seen with all OSCC cell lines tested.

A. Materials and Methods

Human OSCC Cell Lines. The human OSCC cell lines MDA231, PS3, SCC4 and SCC25 were obtained from ATCC (American Type Culture Collection, Rockville, Md.). The HSC3 cell line was obtained from the Japanese Cell Resource Bank (Osaka, Japan). Immortalized non-malignant control keratinocytes, OKF6-TERT2 cells, were obtained from Harvard Medical School Cell Culture Core Collection (Cambridge, Mass.). Cells were maintained in DMEM (GIBCO, Carlsbad, Calif.) supplemented with 10% FBS at 37° C. in 5% CO2. Both cell lines were derived from primary OSCC tumors from the tongues of male patients in their fifth generation of life. Data regarding pertinent medical history, treatment, outcome of care and recurrence were not available.

Animals. Six week-old female athymic nude (nu/nu) mice were purchased from HARLAN Laboratories (Indianapolis, Ind.) and used in a laminar air-flow cabinet under pathogen-free conditions. They were provided with a 12-h light/dark schedule at controlled temperature and humidity with food and water ad libitum. Mice were allowed to acclimate for at least one week prior to the start of the experiments. All procedures were approved by the UTHSCSA (University of Texas Health Science Center—San Antonio) Institutional Animal Care and Use Committee.

OSCC Mouse Xenograft Model. Mice were injected subcutaneously in the right flank with $2 \times 10^6$ HSC3, SCC4, or SCC25 cells in 0.1 ml of sterile phosphate buffered saline (each of these cell lines is published in scientific literature). Four weeks post-inoculation, tumors had grown to an average volume of 110 mm$^3$. Mice were then divided into two experimental groups of five animals each, which received the following treatments as intra-tumoral injections: group A, vehicle control (7% DMSO in sterile saline); group B, CPZ treatment (40 µg). The injections were repeated every other day and for a total of at least 14 days.

Treatments. CPZ (5 mg) was diluted in 250 µl of 100% DMSO to yield a final concentration of 20 µg/µl of stock solution. Stock solution (100 m) was subsequently diluted in 7% DMSO in sterile saline generating a final concentration of 1 µg/µl. A total of 40 µg in 40 µl was injected intra-tumorally. Control xenografts were injected intra-tumorally with 40 µl of vehicle control (7% DMSO). Mice were monitored daily for tumor growth, cachexia, and weight loss. Tumor volumes and body weight were recorded every other day. Tumor volumes were calculated by the formula: $(4\pi/3) \times (w/2)2 \times (l/2)$, where w=width and l=length. Measurements were made using a digital caliper. At the conclusion of the experiments, mice were anaesthetized with isoflurane and cervical dislocation, blood was collected, and the serum was separated and stored at −80° C. until assayed. Biochemical analysis of serum was performed by the Mouse Metabolic Phenotyping Center (Yale School of Medicine, New Haven, Conn.). Tumors were dissected and placed in 10% neutral buffered formalin (SIGMA, St. Louis, Mo.) and processed for histological analysis.

Statistical Analysis. Statistical analyses were performed using GraphPad Prism4 (San Diego, Calif.). Experiments were performed in triplicate and results are represented as means+SD except when indicated. QPCR of TRPV1 expression was analyzed using one-way analysis of variance (ANOVA) with Tukey's post-hoc test (n=3). Cytotoxicity assays of cell viability were analyzed by one-way ANOVA and Bonferroni's post-hoc test (n=3). Calcium imaging of OSCC cell lines were analyzed by two-way ANOVA with Bonferroni's post-hoc test (n=3). Statistical analyses of tumor growth were made using analysis of variance with repeated measures with Bonferroni's post-hoc test (n=5). Student's t-test was used to evaluate TUNEL staining of apoptotic figures (n=3; six fields per section) in treated vs. control xenografts. A p value less than 0.05 was considered statistically significant.

B. Results and Discussion

Figure 4:
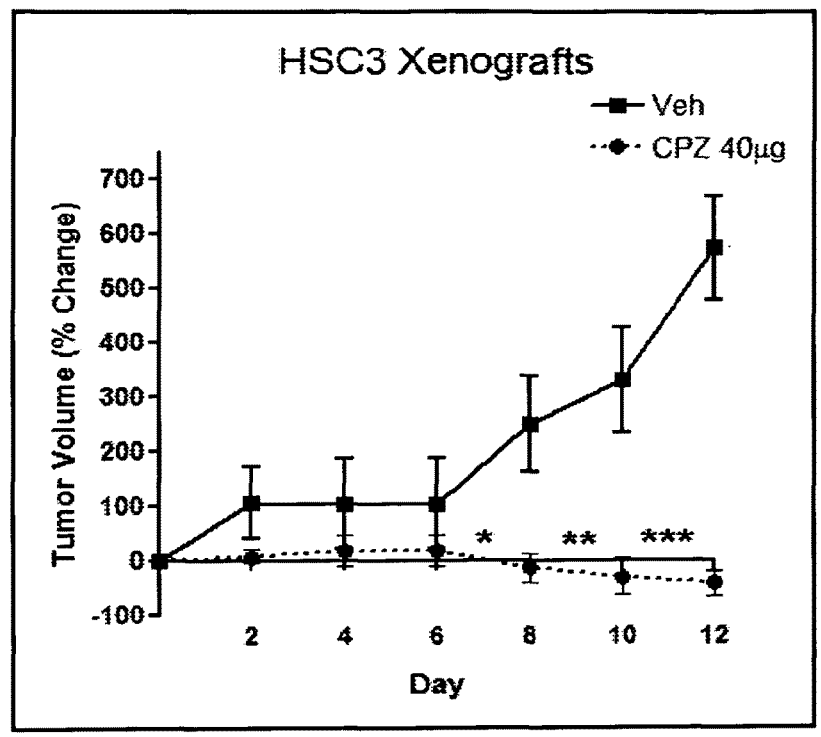
Figure 5:
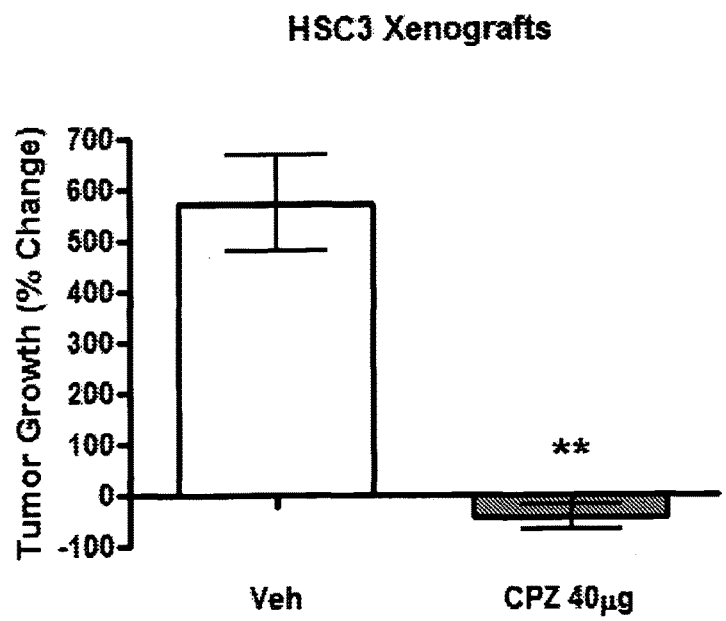
Figure 8:
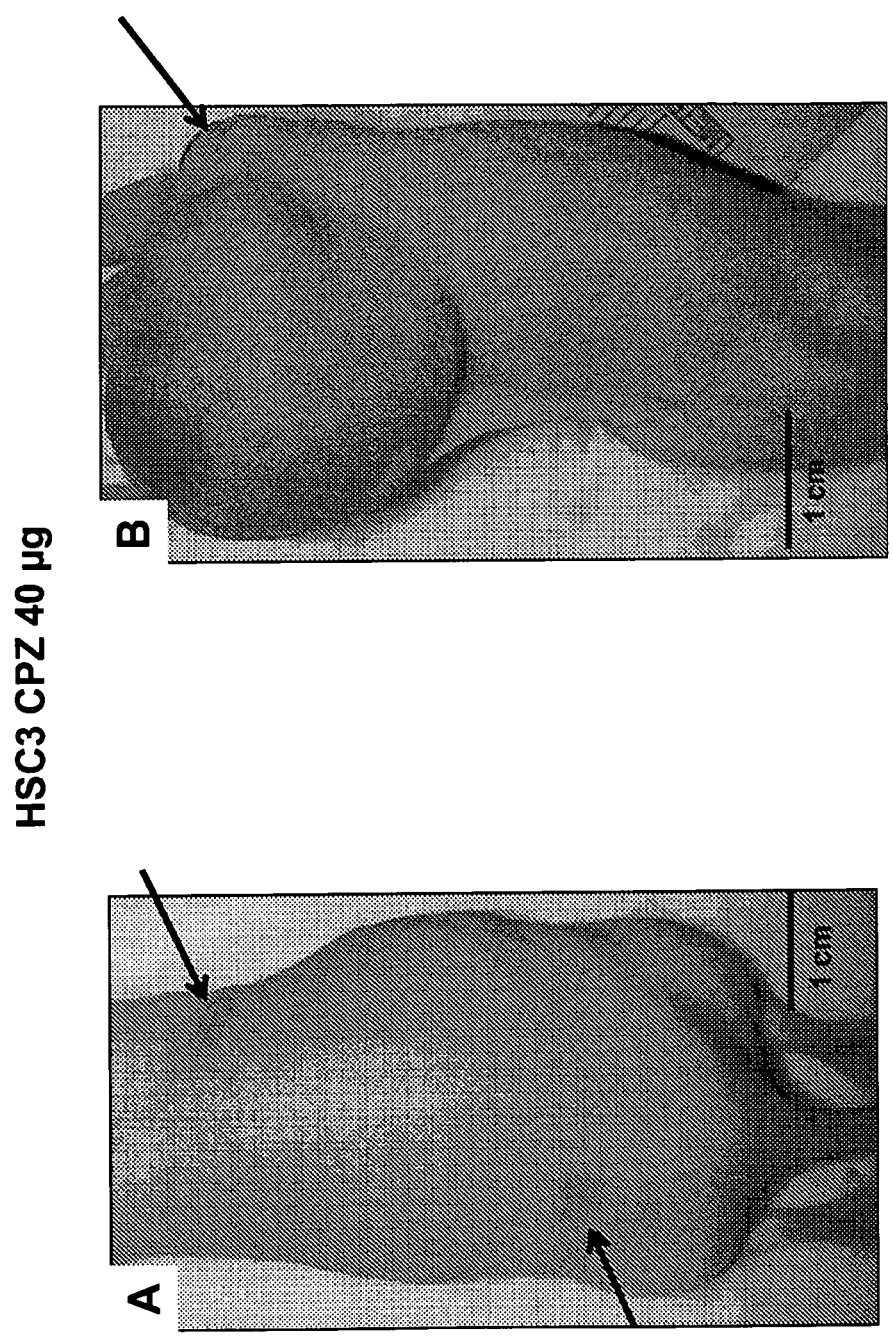
FIG. 8. HSC3 xenografts treated with 40 μg CPZ (arrows), i.e., CPZ 40 μg=40 μg CPZ in 40 μl Veh medium (1 μg/μl) injected directly into tumor every other day. Panel A. Healed HSC3 xenograft treated with 40 μg CPZ. Panel B: Mouse with one control treated HSC3 xenograft and one CPZ treated HSC3 xenograft (arrow).
Figure 9:
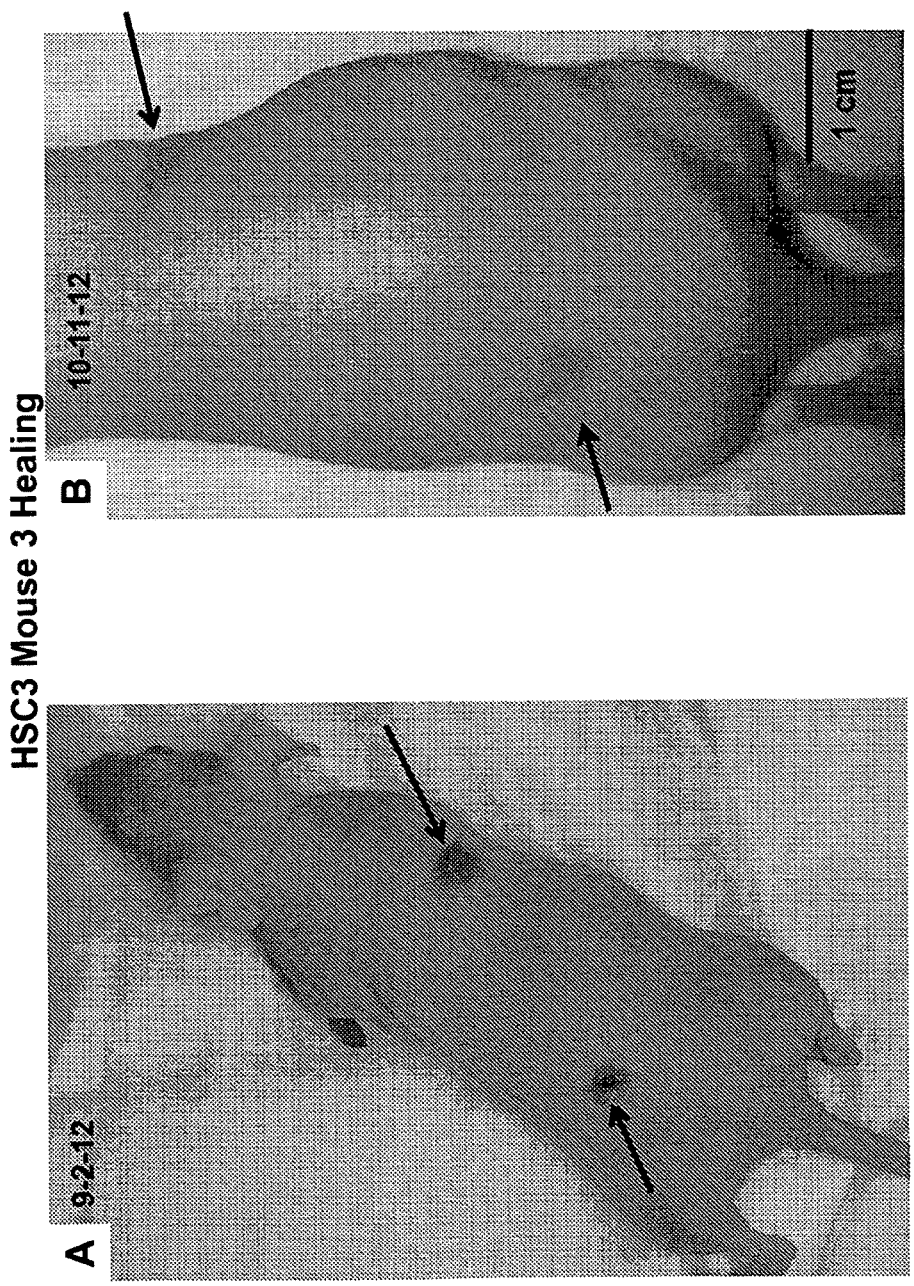
FIG. 9. Two HSC3 xenografts healing in "Mouse 3" following treatment with 40 μg CPZ in 40 μl Veh medium (1 μg/μl) injected directly into the tumor every other day. Panel A: Healing following eight days treatment with bulk of tumor having fallen off but with remaining wounds. Panel B: Additional healing for five weeks following tumor necrosis and wound closure.
Figure 10:
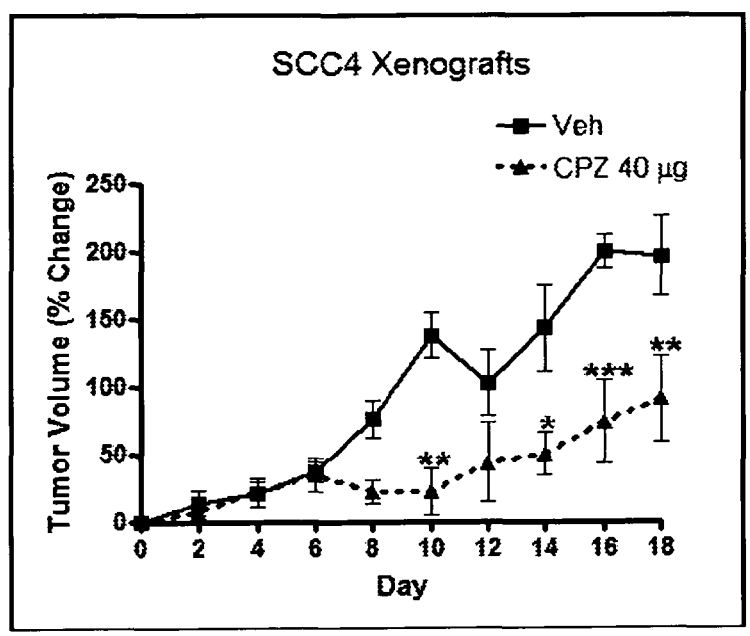
FIG. 10. SCC4 xenografts from experiment #1. Tumor growth (% change) over 22 days. Veh=delivery vehicle control without CPZ; CPZ 40 μg=40 μg CPZ in 40 μl Veh medium (1 μg/μl) injected directly into the tumor every other day. *p<0.05, **p<0.01.
Figure 11A:
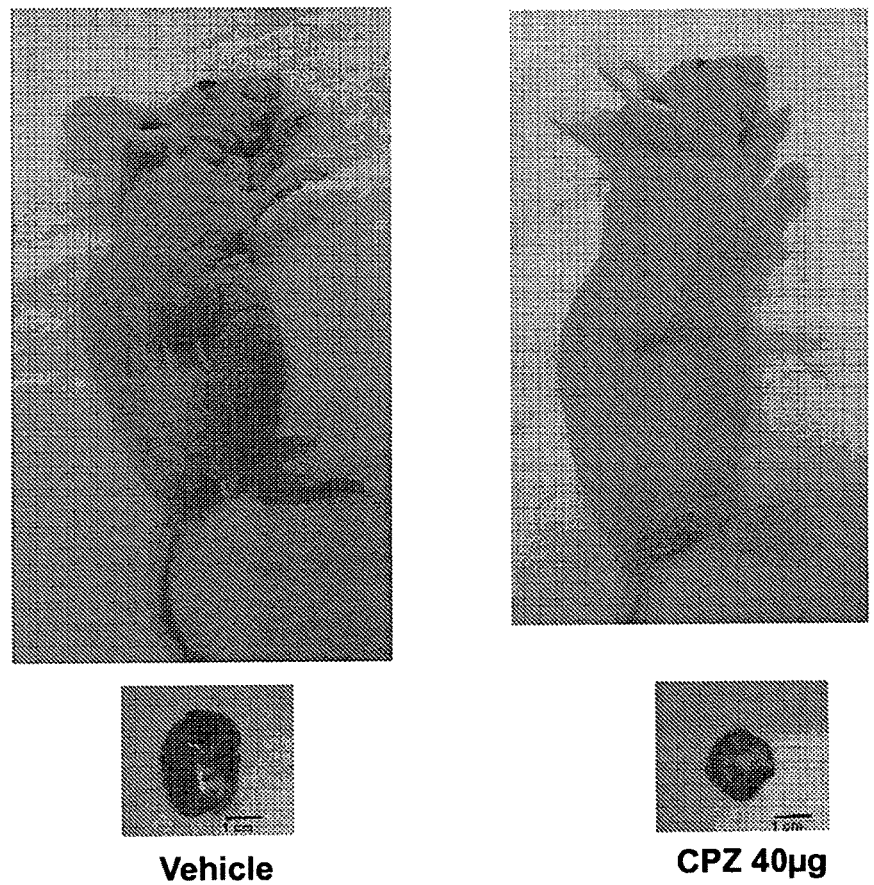
FIG. 11A. SCC4 xenografts from experiment #2. Vehicle and 40 μg CPZ ("CPZ 40 μg") treated xenografts following two weeks of treatment. Vehicle=delivery vehicle control without CPZ; CPZ 40 μg=40 μg CPZ in 40 μl Veh medium (1 μg/μl) injected directly into tumor every other day.
Figure 11B:
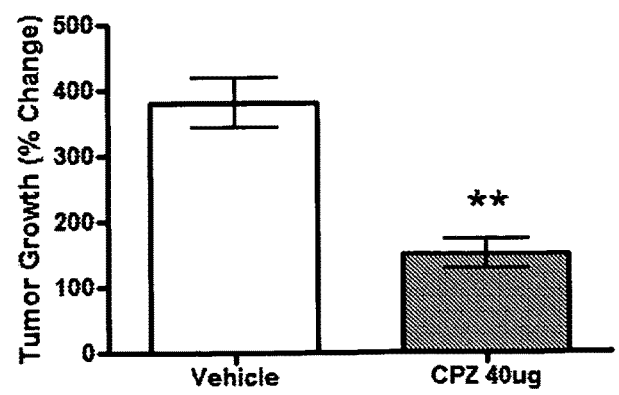
FIG. 11B: SCC4 xenografts from experiment #2. Overall tumor growth (% change) over 14 days; Vehicle=delivery vehicle control without CPZ; CPZ 40 μg=40 μg CPZ in 40 μl Veh medium (1 μg/μl) injected directly into tumor every other day. **p<0.01.

Results on assessing the utility of CPZ in treating OSCC in vivo were promising. The OSCC xenografts (HSC3, SCC4 and SCC25) that were generated in athymic nude mice (n=5) (FIGS. 4, 5, 6-9, 10, 11A, 11B, 12A, 12B, and 13) and that were treated with 40 µg CPZ (1 µg/µl) (FIGS. 4, 5, 6-9, 10, 11A and 11B) [or 20 µg CPZ (1 µg/µl) (FIGS. 12A. 12B, and 13)] or vehicle control (40 µl [or 20 µl] 7% DMSO) every other day for a period of two weeks showed a dramatic response to treatment with CPZ, which resulted in either a significant reduction in tumor growth rate (SCC4; p<0.05) or a significant reduction in tumor volume (HSC3 and SCC25; p<0.05) with complete healing in some treated HSC3 xenografts (FIG. 9; see also FIGS. 4 & 5). Nearly complete healing was observed in treated SCC25 xenografts (FIGS. 12A & 12B), while a significant reduction was observed in cancerous tumor cell growth rate in treated SCC4 xenografts (FIGS. 10, 11A, and 11B). In general, the mice did not lose weight, and they resumed normal motor function following each treatment throughout the approximately two-week treatment period.

Figure 6:
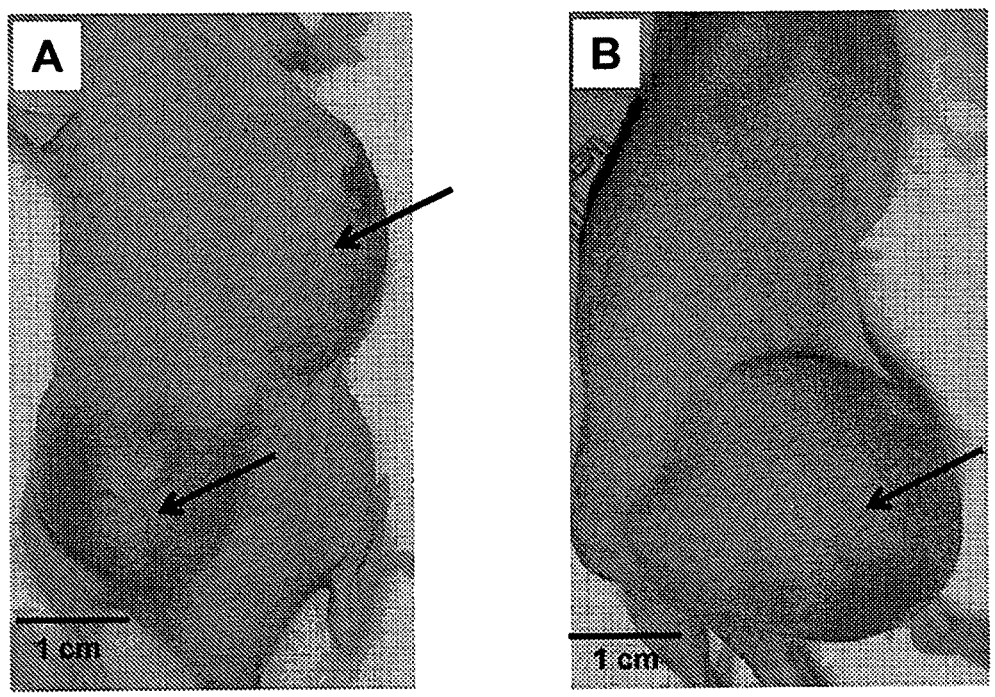
Figure 7:
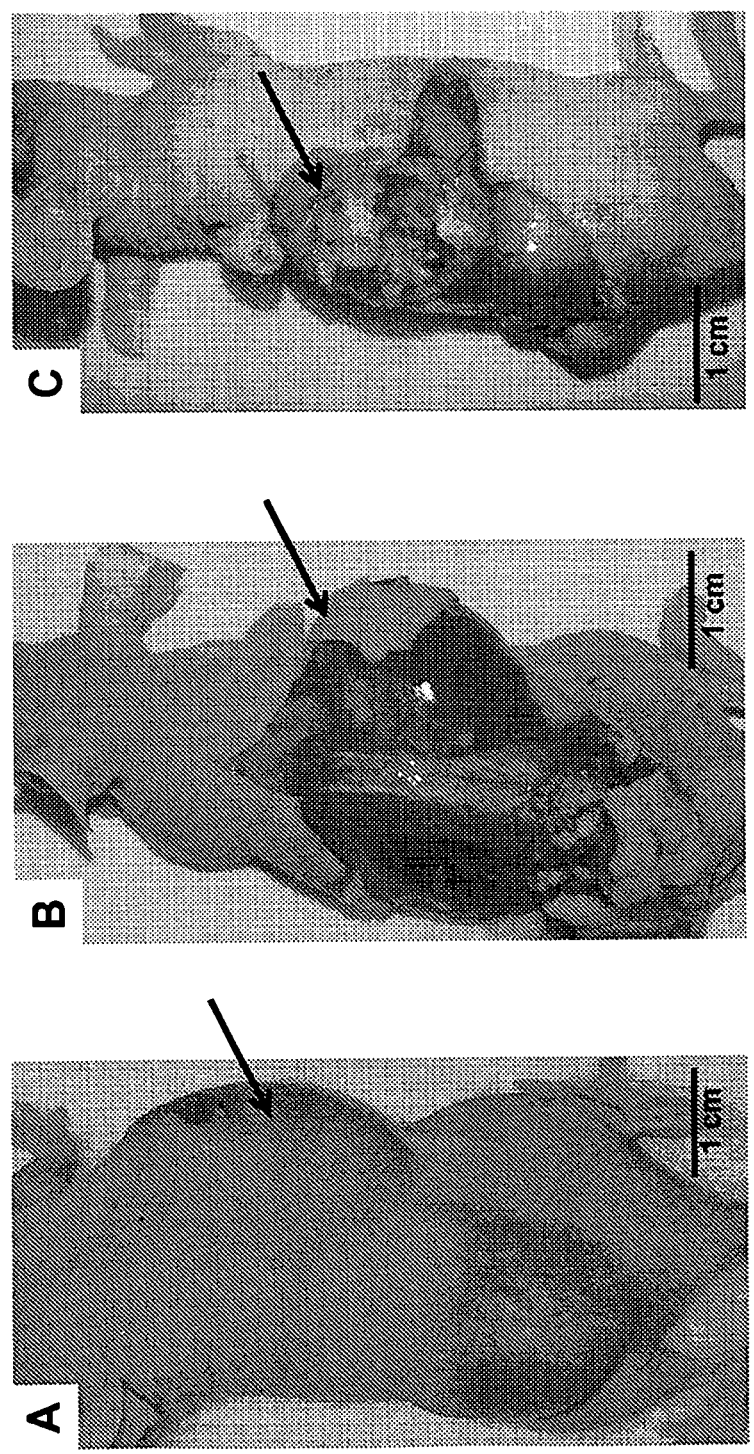
FIG. 7. HSC3 control xenografts (arrows). Panel A: HSC3 control xenograft before dissection. Panel B: Fluid-filled HSC3 control xenograft prior to incision. Panel C: Incised HSC3 control xenograft demonstrating fluid-filled sac containing HSC3 tumor cells that have eroded into the peritoneal cavity.

HSC3 xenografts initially displayed an exophytic solid tumor mass that was highly vascularized. By day 8, control tumors grew significantly in size and were no longer a solid mass, rather they also contained fluid which was palpable (FIGS. 6 & 7). However, treated tumors failed to become very large and fluid filled and, in fact, dramatically shrank in size and in some cases healed. Complete healing at the tumor sites was seen, with remaining scars being indicative of the initial tumor that was present (FIGS. 8 & 9). Upon sacrifice and dissection, HSC3 xenografts were determined to be extremely metastatic; the "fluid filled sacs" were found to be due to the tumors eroding into the peritoneal cavity. These "sacs" contained a large amount of tumor cells (FIG. 7). One animal had a tumor that was treated on the left hind flank and an untreated tumor that received vehicle control on the right hind flank (FIG. 8, Panel B; tail end of animal is oriented toward top of Panel B, so that the right hind flank appears on the upper left in Panel B). The dramatic difference in tumor volumes following 12 days of treatment is evident (FIG. 8, Panel B). Complete healing of two HSC3 tumor xenografts following 14 days of treatment, with additional time for wound healing after each tumor had terminated, is shown in FIG. 9.

SCC4 xenografts were fast growing solid exophytic tumors that failed to metastasize. Approximately 4 treatments (eight days) were required before changes in tumor growth rates were evident (experiment #1 FIG. 10—tracked for 22 days). By day eight, significant changes in tumor growth were seen, and by day sixteen, vehicle-control-treated tumors had grown two-fold greater than those treated with 40 µg CPZ (p<0.01) (see FIG. 10; and see also experiment #2 of FIGS. 11A & 11B). Repeat experiments treating with 60 μg CPZ revealed a 3 fold difference in tumor growth rates between vehicle control and treated mice (data not shown).

Figure 12A:
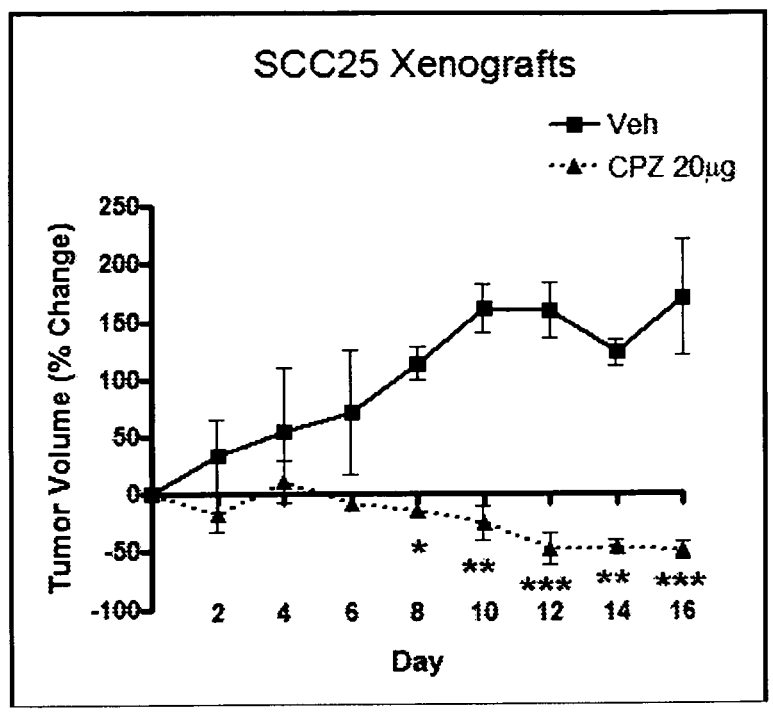
FIG. 12A. SCC25 xenografts (over 16 days). Tumor growth (% change) over 16 days. Veh=delivery vehicle control without CPZ; CPZ 20 μg=20 μg CPZ in 20 μl Veh medium (1 μg/μl) injected directly into tumor every other day. *p<0.05; **p<0.01.
Figure 12B:
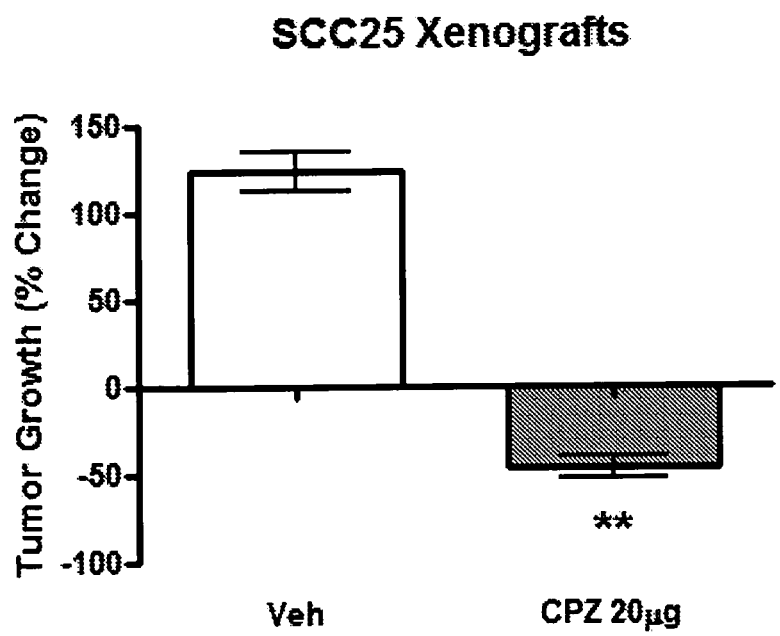
FIG. 12B. SCC25 xenografts (at day 14). Overall tumor growth (% change). Veh=delivery vehicle control without CPZ; CPZ 20 μg=20 μg CPZ in 20 μl Veh medium (1 μg/μl) injected directly into tumor every other day. **p<0.01.
Figure 13:
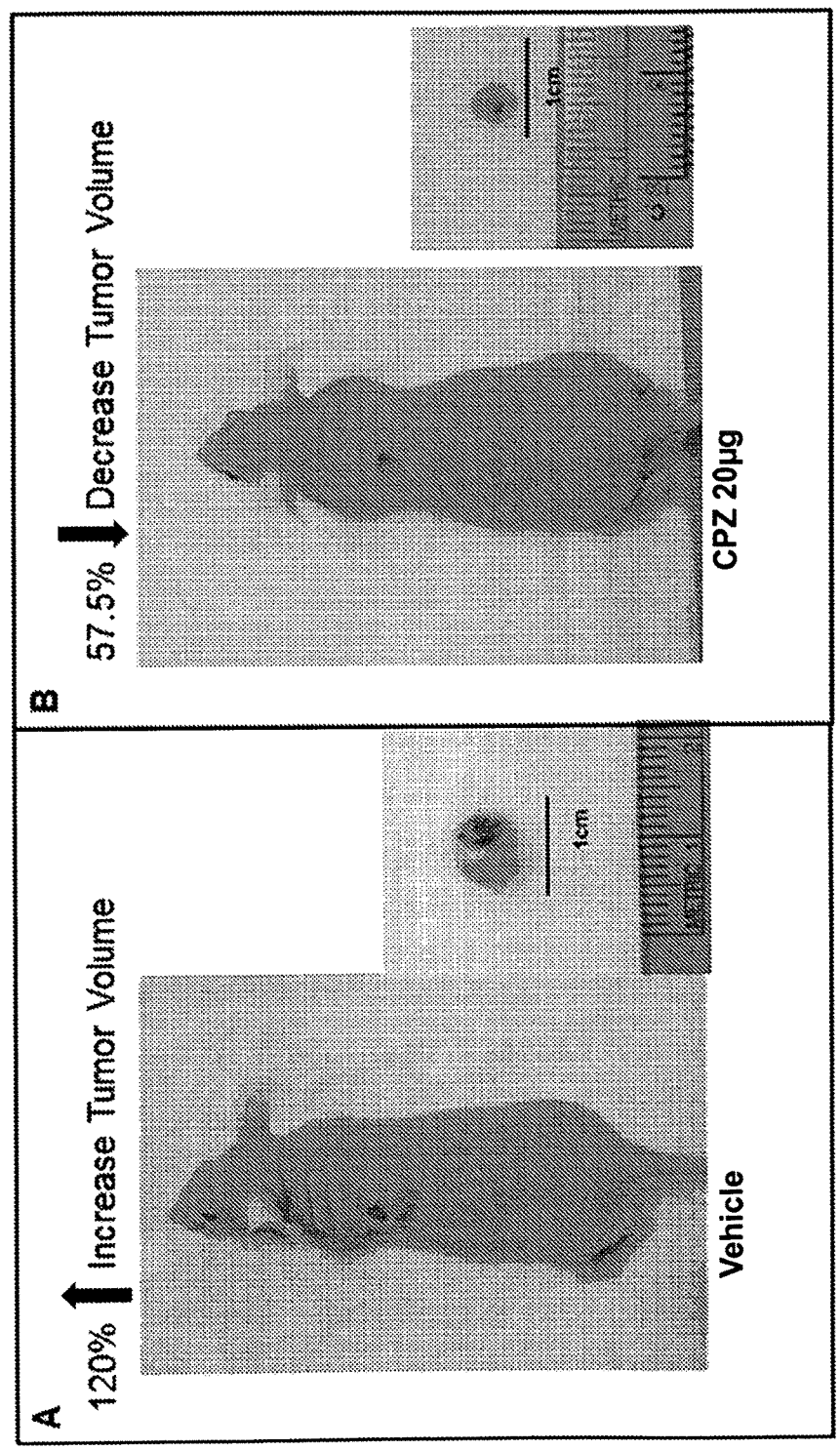
FIG. 13. SCC25 xenografts (separate experiment from experiment of FIGS. 12A & 12B). Panel A: SCC25 xenograft treated with vehicle control for two weeks; 120% increase in tumor volume. Panel B: SCC25 xenograft treated with 20 μg CPZ (1 μg/μl) injections over two weeks; 57.5% decrease in tumor volume.

SCC25 xenografts were slow growing exophytic solid tumors that failed to metastasize. These xenografts displayed a dramatic reduction in tumor volume following treatment with 20 μg CPZ (1 μg/μl) (FIGS. 12A, 12B & 13).

At the conclusion of the experiment, serum was collected for liver and kidney function analysis. No negative effects on liver or kidney function were detected (FIG. 14). Tumors were analyzed histologically using H&E (hematoxylin and eosin) and TUNEL (terminal deoxyribonucleotidyl transferase-mediated dUTP nick end labeling) staining for detection of DNA fragmentation associated with apoptosis, and apoptotic figures were quantified. [FIGS. 15-1 to 15-3] A significant increase in apoptotic figures in treated tumors (p<0.001) was found, which positively corresponds with cell culture studies. In summary, these findings demonstrate that CPZ effectively slows, reverses, and even terminates OSCC tumor growth without the negative side effects associated with administration of CAP (e.g., pain and ulceration). Therefore, CPZ empirically has shown promise for being a well-tolerated treatment for OSCC.

Example 2

Additional In Vitro Studies

Additional cell proliferation assays using OSCC cell lines (SCC4, SCC25, Cal27, and HSC3), the breast cancer cell line MDA231, and the prostate cancer cell line LnCap have demonstrated that treatment with CPZ brings about a significant reduction in cell proliferation following 24 hour treatment. Observed reductions in cell proliferation in these additional in vitro studies are as follows: SCC4, 40%; HSC3, 50%; SCC25, 80%; Cal27, 15%; MDA231, 56%; and LnCap, 37%.

Example 4

ROS Assays

ROS levels in OSCC cell lines were examined by flow cytometry using 2,7-dichlorodihydrofluorescein diacetate (DCF-DA; Sigma-Aldrich, St. Louis, Mo.). Cells ($3\times10^5$) were plated in 12-well plates and incubated for 30 min with DCF-DA at 37° C. then treated with 30 μM capsazepine using phenol free media with and without 10 mM NAC. Treated cells were incubated for 1 h at 37° C., harvested, washed twice, and analyzed by FACS. Results are shown in FIGS. 1I-1 to 1I-6.

Example 4

Body Temperature Regulation

TRPV1 is known to regulate body temperature with TRPV1 agonists inducing pronounced hypothermia and TRPV1 antagonists inducing pronounced hyperthermia. Local treatment of OSCC through intra-tumoral injections with a TRPV1 antagonist like CPZ has promise for circumventing body temperature modulation mediated through TRPV1-agonist-or TRPV1-antagonist effects on the central nervous system.

A TRPV1 antagonist has been tested using oral administration for the ability to block pain in a number of phase I clinical trials and was shown to induce hyperthermia. Specifically, the Amgen compound, AMG 517, was discontinued due to pronounced hyperthermia (up to 1.5° C. hyperthermia seen at 0.3-3 mg/kg) (Gunthorpe & Chizh, 2008). The occurrence of ~3° C. increases was seen at doses of 2 mg in one patient. Research by Gavva et al., 2007 has defined a key role of tonic TRPV1 receptor activity in thermoregulation with many clinically distinct TRPV1 antagonists causing hyperthermia, typically in the range of 0.5-1.5° C., in preclinical species such as rat, mouse, dog, and monkey. Gunthorpe & Chizh at 64.

To the extent CPZ or an analog thereof may similarly effect body temperature regulation, local delivery, including by injection, of a composition comprising CPZ or an analog of CPZ would allow for administration of higher doses with lower overall systemic effects—such as changes in body temperature. Use of liposomal, polymer, nanoparticle or other formulations to inhibit migration of the composition from the tumor would further serve to reduce systemic effects.

Notwithstanding the pronounced hyperthermia that has been reported in studies involving administration of some TRPV1 antagonists for systemic distribution, some embodiments of this invention include systemic administration. Studies involving intravenous administration of CPZ for analgesic use (Garami et al, 2010) demonstrated that, unlike other TRPV1 antagonists, CPZ does not cause hyperthermia in a rat model at a high intravenous administration dose. Furthermore, cell viability assays conducted by the inventor demonstrate that CPZ induces cell death in cancer cell lines but does not induce death of normal, non-malignant oral keratinocytes. No inflammation, ulceration, necrosis or pain were evident in adjacent healthy tissues in tumor bearing mice treated by intratumoral injection with CPZ. Liver and kidney function tests of tumor bearing mice treated by intratumoral injection with CPZ did not demonstrate negative effects on liver or kidney function. Use of CPZ (and its analogs) by systemic administration may allow treatment of metastatic cancers and primary cancers that are not readily accessible for direct injection.

Example 5

Treatment to Simultaneously Halt Cancer Growth and Block Pain

Studies indicate that CPZ has no negative effects on non-cancerous tissues, and, because it is a TRPV1 antagonist, it blocks pain that is generated through activation of TPRV1 channels. The possibility of alleviating pain through administration of a composition comprising CPZ or an analog of CPZ may be particularly opportune in that many receptor mechanisms and regulatory pathways implicated in pain signaling demonstrate a level of convergence onto TRPV1 (Gunthorpe & Chizh, 2008) Therefore, treatment of a cancerous tumor by administration of a composition comprising CPZ or an analog of CPZ into tumors offers a novel, effective, well-tolerated therapy not only for halting cancer cell growth, e.g., in OSCC tumors, but also to block pain.

Tumors of oral cancer patients frequently are inoperable because they invade, or are approximated upon, critical structures in the head and neck. For example, many OSCC patients exsanguinate due to inoperable involvement of the tumor with the carotid artery. But through administration of a composition comprising CPZ or an analog of CPZ, treatment of an OSCC patient in which critical structures are invaded can nonetheless be completed, without potentially fatal complications, and with the possibility of subsequent surgical intervention following this treatment (e.g., after tumor shrinkage is brought about through administration of a composition comprising CPZ or an analog of CPZ). Administration, such as by direct, intra-tumoral injection, of a composition comprising CPZ or an analog of CPZ into tumors before critical structures are invaded can also prevent tumor invasion, e.g., of nerve bundles and other critical structures such as the carotid artery.

Patients with inoperable tumors in the head and neck often experience intense pain as the tumors grow and invade critical structures. As these tumors grow, they frequently invade neurovascular structures (resulting in pain intensification) and they often rupture the carotid artery (resulting in death). Opioids are the main drugs used to manage this pain and to provide some palliative care. However, patients may quickly develop tolerance to opioid drugs and experience little to no pain management. Often a very slow and painful death may result. Treatment with CPZ offers these patients the benefit of retarding the tumor's growth and potentially preventing invasion of critical structures. It also offers the added benefit of alleviating pain by blocking TRPV1 channels that are highly expressed in pain sensing neurons found in the head and neck.

In summary, treatment of a composition comprising CPZ or an analog of CPZ consequently promises to be useful in halting the growth of cancers (e.g., head and neck cancer) while potentially simultaneously blocking pain (e.g., in head and neck cancer patients). Treatment can be systemic or local. According to some embodiments of the invention, systemic administration of CPZ or an analog of CPZ may be obviated through direct injection into tumors, and yet effective pain management nonetheless may be achieved.

While discussed above in the context of oral cancer cells and tumors affecting the head and neck region, administration of compositions comprising CPZ or analogs thereof can also be used to treat cervical cancer, prostate cancer, or breast cancer while simultaneously blocking pain. CPZ-mediated reduction in tumor volume and potential simultaneous blockage of pain-sensing TRPV1 channels offers the possibility of a prolonged life expectancy, a halting in the growth of a tumor, a reduction in tumor volume for surgical resection, providing a better quality of life to many patients, and/or may be useful for palliative care.

REFERENCES

The following references, to the extent that they provide exemplary procedural or other details supplementary to those set forth herein, are each specifically herein incorporated by reference in the entirety of each.

American Cancer Society, Cancer Facts and Figures 2012 (Retrieved Nov. 5, 2012 from http://www.cancer.org/Research/CancerFactsFigures/ACSPC-031941)
Chizh et al. *American Pain Society Meeting*, Poster #765, 2006.
Culshaw et al., *J. Med. Chem.* 49:471-474, 2006.
Deeds, et al., *Hum. Pathol.* 31: 1346-1356, 2000.
Docherty, et al., *Br. J. Pharmacol.* 121: 1461-1467, 1997.
Domotor, et al., *Inflammopharmacology* 13: 161-177, 2005.
Duncan, et al., *J. Clin. Oncol.* 19: 568-576, 2001.
Duncan, et. al., *Cancer Res.* 58: 1515-1520, 1998.
Fang & Setaluri, *Biochem. Biophys. Res. Commun.* 279: 53-61, 2000.
Fixemer, et al., *Oncogene* 22: 7858-7861, 2003.
Fuessel, et al., *Int. J. Oncol.* 23: 221-228, 2003.
Garami et al., *J. of Neuroscience.* 30: 1435-1440, 2010.
Gavva et al., *J. Neurosci.* 27: 7459-7468, 2007.
Gavva et al., *J. Pharmacol. Exp. Ther.* 313: 474-484, 2005.
Ghilardi et al., *J. Neurosci.* 25: 3126-3131, 2005.
Gunthorpe & Chizh, *Drug Discovery Today* 14: 56-67, 60-61, 2008
Hartel, et al., *Gut.* 55: 519-528, 2006.
Honore et al., *J. Pharmacol. Exp. Ther.* 314: 410-421, 2005.
Kouhen, et al., *J. Pharmacol. Exp. Ther.* 314: 400-409, 2005.
Lazzeri, et al., *Eur. Urol.* 48: 691-698, 2005.
Liu & Simon, *Neurosci. Lett.* 228: 29-32, 1997.
Mergler, et al., *Neuroendocrinology* 85: 81-92, 2007.
Ornyanov et al., *J. Med. Chem.* 49: 3719-3742, 2006.
Peng, et al., *Biochem. Biophys. Res. Commun.* 278: 326-332, 2000.
Peng, et al., *Biochem. Biophys. Res. Commun.* 282: 729-734, 2001.
Pomonis et al., *J. Pharmacol. Exp. Ther.* 306: 387-393, 2003.
Prevarskaya, et al., *Biochica et Biophysica Acta.* 1772: 937-46, 2007a.
Prevarskaya, et al., *Cell Death and Differentiation* 14: 1295-1304, 2007b.
Rami et al., *Bioorg. Med. Chem. Lett.* 16: 3287-3291, 2006.
Reilly, et al., *Toxicol Sci.* 73(1): 170-81, 2003.
Sanchez, et al., *Eur. J. Pharmacol.* 515: 20-27, 2005.
Swanson et al. *J. Med. Chem.* 48: 1857-1872, 2005.
Szallasi & Appendino, *J Med Chem.* 47: 2717-2723, 2004
Szallasi, et al., *Nature Reviews Drug Discovery* 6: 357-372, 2007
Tominaga & Malmberg, *Neuron* 21: 531-543, 1998.
Tsavaler, et al., *Cancer Res.* 61: 3760-3769, 2001.
Velanzano et al., *J. Pharmacol. Exp. Ther.* 306: 377-386, 2003.
Walker et al., *J. Pharmacol. Exp. Ther.* 304: 56-62, 2003.
Walpole et al., *J. Med. Chem.* 37: 1942-1954, 1994.
Weil, et al., *Mol. Pharmacol.* 68: 518-527, 2005.
Wissenbach, et al., *Biochem. Biophys. Res. Commun.* 322: 1359-1363, 2004.
Zheng et al., *The 232$^{nd}$ ACS National Meeting*, San Francisco, Calif. Sep. 10-14, 2006.
Zhuang, et al., *Lab. Invest.* 82: 1755-176, 2002.
Ziglioli, et al., *Acta Biomed.* 80: 13-20, 2009.

The invention claimed is:

1. A method for reducing cancerous tumor cell growth, the method comprising administering an effective amount of a composition comprising capsazepine or an analog of capsazepine to a subject having or suspected of having cancerous tumor cell growth, wherein the cancerous tumor cell growth is oral squamous cell carcinoma, head and neck cancer, breast cancer, or cervical cancer.

2. The method of claim 1, wherein the subject has been diagnosed with a cancerous solid tumor.

3. The method of claim 1, wherein the composition comprising capsazepine or an analog of capsazepine is administered by injection intratumorally.

4. The method of claim 1, wherein the composition comprising capsazepine or an analog of capsazepine is administered for distribution systemically within the subject.

5. The method of claim 1, wherein the composition comprising capsazepine or an analog of capsazepine further comprises a pharmaceutically acceptable carrier or diluent.

6. The method of claim 5, wherein the pharmaceutically acceptable carrier or diluent is DMSO.

7. The method of claim 1, wherein the subject is administered a composition comprising capsazepine or an analog of capsazepine and a composition comprising a second active agent.

8. The method of claim 7, wherein the second active agent is an inhibitor of Coenzyme Q.

9. The method of claim 7, wherein the composition comprising capsazepine or an analog of capsazepine is administered at the same time as the composition comprising the second active agent.

10. The method of claim 7, wherein the composition comprising capazepine or an analog of capsazepine is administered before or after the composition comprising the second active agent is administered.

11. The method of claim 10, wherein the interval of time between administration of the composition comprising capsazepine or an analog of capsazepine and the composition comprising the second active agent is 1 to 30 days.

12. The method of claim 1, wherein the subject is a mammal.

13. The method of claim 1, wherein the subject is a human.

14. The method of claim 1 for alleviating pain in the subject associated with the cancerous tumor cell growth.

15. The method of claim 1, wherein the composition comprising capsazepine or an analog of capsazepine reduces cancerous tumor cell growth in the subject in a TRPV1 independent manner.

16. The method of claim 1, wherein an effective amount of a composition comprising capsazepine or an analog of capsazepine is administered to a subject having or suspected of having cancerous tumor cell growth without inducing either pronounced hypothermia or pronounced hyperthermia in the subject.

17. The method of claim 1, wherein an effective amount of a composition comprising capsazepine or an analog of capsazepine is administered as palliative care to a subject having or suspected of having cancerous tumor cell growth.

* * * * *